(12) United States Patent
Lok

(10) Patent No.: US 10,385,334 B2
(45) Date of Patent: Aug. 20, 2019

(54) MOLECULAR IDENTITY TAGS AND USES THEREOF IN IDENTIFYING INTERMOLECULAR LIGATION PRODUCTS

(71) Applicant: Si Lok, Hong Kong (CN)

(72) Inventor: Si Lok, Hong Kong (CN)

(*) Notice: Subject to any disclaimer, the term of this patent is extended or adjusted under 35 U.S.C. 154(b) by 560 days.

(21) Appl. No.: 14/894,653

(22) PCT Filed: May 30, 2014

(86) PCT No.: PCT/IB2014/061855
§ 371 (c)(1),
(2) Date: Nov. 30, 2015

(87) PCT Pub. No.: WO2014/191976
PCT Pub. Date: Dec. 4, 2014

(65) Prior Publication Data
US 2016/0108394 A1 Apr. 21, 2016

Related U.S. Application Data

(60) Provisional application No. 61/956,050, filed on May 31, 2013.

(51) Int. Cl.
| | | |
|---|---|---|
| *C12Q 1/6855* | (2018.01) | |
| *C12N 15/10* | (2006.01) | |
| *C07H 21/00* | (2006.01) | |
| *C40B 70/00* | (2006.01) | |
| *C12N 15/64* | (2006.01) | |
| *C12N 15/66* | (2006.01) | |
| *C40B 20/04* | (2006.01) | |
| *C40B 50/06* | (2006.01) | |

(52) U.S. Cl.
CPC ......... *C12N 15/1065* (2013.01); *C07H 21/00* (2013.01); *C12N 15/10* (2013.01); *C12N 15/64* (2013.01); *C12N 15/66* (2013.01); *C12Q 1/6855* (2013.01); *C40B 70/00* (2013.01); *B01J 2219/00572* (2013.01); *B01J 2219/00722* (2013.01); *C40B 20/04* (2013.01); *C40B 50/06* (2013.01)

(58) Field of Classification Search
None
See application file for complete search history.

(56) References Cited

U.S. PATENT DOCUMENTS

| | | |
|---|---|---|
| 5,695,937 A | 12/1997 | Kinzler et al. |
| 5,830,645 A | 11/1998 | Pinkel et al. |
| 5,874,259 A | 2/1999 | Szybalski |
| 6,159,685 A | 12/2000 | Pinkel et al. |
| 6,709,861 B2 | 3/2004 | Mead et al. |
| 6,730,500 B1 | 5/2004 | Lok |
| 7,932,029 B1 | 4/2011 | Lok |
| 8,329,400 B2 | 12/2012 | Lok |
| 2006/0292611 A1 | 12/2006 | Berka et al. |
| 2011/0160078 A1 | 6/2011 | Fodor et al. |

FOREIGN PATENT DOCUMENTS

WO 2016/105199 A1 6/2016

OTHER PUBLICATIONS

Jarvie, T. et al. "De Novo Assembly and Genomic Structural Variation Analysis with Genome Sequencer FLX 3K Long-Tag Paired End Reads," (2008) BioTechniques 44(6):829-831.
Korbel, J.O. et al., "Paired-End Mapping Reveals Extensive Structural Variation in the Human Genome," (2007) Science 318:420-426 (and supporting materials).
Maretty, L. et al., "Sequencing and de novo assembly of 150 genomes from Denmark as a population reference," (2017) Research Letter, Nature, 000:1-19.
Albertson, et al., 2003. Genomic microarrays in human genetic disease and cancer. *Hum Mol Gen* 12 Spec No. 2: R145-R152.
Albertson, et al, 2000. Quantitative mapping of amplicon structure by array CGH identifies CYP24 as a candidate oncogene. *Nat Genet* 25: 144-1.
Andersson L, 2001. Genetic dissection of phenotypic diversity in farm animals. *Nat Rev* 2: 130-138.
Ausubel et al. (eds.), Short Protocols in Molecular Biology, 3rd Ed, John Wiley & Sons, New York, 1995 Book—Not Provided.
Bailey, et al., 2002. Recent segmental duplications in the human genome. *Science* 297: 1003-1007.
Barren and Lai, Pulse Field Electrophoresis: A Practical, Academic Press, San Diego, 1993 Book—Not Provided.
Batzoglou, et al, 2002. ARACHNE: A whole-genome shotgun assembler. *Genome Res* 12: 177-189.
Bignell, et al., 2004. High-resolution analysis of DNA copy number using oligonucleotide microarrays. Genome Res 14: 287-295.
Birren et al., Bacterial Artificial Chromosomes in Genome Analysis—A Laboratory Manual, CSH Press, New York, 1999 Book—Not Provided.

(Continued)

*Primary Examiner* — Christopher M Gross
(74) *Attorney, Agent, or Firm* — Daniel A. Blasiole; DeWitt LLP

(57) ABSTRACT

Molecular identity tags and methods of marking target nucleic acids with molecular identity tags for identifying intermolecular ligation products. Terminal regions of linear target nucleic acids are marked with pairs of distinguishable molecular identity tags. Each linear target nucleic acid is marked with only one distinguishable pair. The terminal ends of the marked target nucleic acids are joined to generate circularized nucleic acids, thereby juxtaposing two molecular identity tags across the joined terminal ends. Circularized nucleic acids or downstream products thereof comprising juxtaposed unpaired molecular identity tags constitute intermolecular nucleic acid products that can be identified and eliminated from subsequent analyses of the nucleic acids. The molecular identity tags may comprise physically linked and non-physically linked pairs. Physically linked molecular identity tags designed for production and analysis of mate-pair libraries with next-generation sequencing platforms are provided.

19 Claims, 9 Drawing Sheets
Specification includes a Sequence Listing.

(56) References Cited

OTHER PUBLICATIONS

Bolivar et al., 1977. Construction and characterization of new cloning vehicles. II multipurpose system. *Gene* 2: 95-113.
Brennan, et al., 2004. High-resolution global profiling of genomic alterations with long oligonucleotide microarray. *Cancer Res* 64: 4744-4748.
Bujnicki, JM, 2001. Understanding the evolution of restriction-modification systems: Clues from sequence and structure comparisons. *Acta Biochimica Polonica* 48: 935-967.
Buryanov, et al., 1978. Site specific and chromatographics properties of *E coli* K12 and Eco RII DNA-cytosine methylases. *FEBS Lett* 88: 251-254.
Chang et al., 1978. Construction and characterization of amplifiable multicopy DNA cloning vehicles derived from the P15A cryptic miniplasmid. *J Bacteriology* 134: 1141-1156.
Check, E., 2005. Patchwork people. *Nature* 437: 1084-1096.
Cheng, et al., 2005. A genome-wide comparison of recent chimpanzee and human segmental duplications. *Nature* 437: 88-93.
Collins, et al., 1984. Directional cloning of DNA fragments at a large distance from an initial probe: A circularization method. *Proc Natl Acad Sci* (USA) 81: 6812-6816.
Collins et al, 1987. Construction of a general human chromosome-jumping library, with application in cystic fibrosis. *Science* 235: 1046-1049.
Craddock et al., 2001. Molecular genetics of bipolar disorder. *Br J Psychiatry* Suppl 41: S128- S133.
Craig et al., Identification of genetic variants using barcoded multiplexed sequencing, Nature Methods 5:887-893, 2008.
Deininger PL, 1983. Random subcloning of sonicated DNA: Application to shotgun DNA sequence analysis. *Analvt Biochem* 129: 216-223.
Dugaiczyk et al., 1975. Ligation of Eco RI endonuclease-generated DNA fragments into linear and circular structures. *J Mol Biol* 96: 171-178.
Dunn, et al., 2002. Genomic signature tags (GSTs): A system for profiling genomics DNA. *Genome Res* 12: 1756-1765.
Edgren et al., Identification of fusion genes in breast cancer by paired-end RNA-sequencing, Genome Biol 12:R6, 2011.
Edwards, et al., 1990. Automated DNA sequencing of the human HPRT locus. *Genomics* 6: 593-608.
Feng et al, 2002. Increased efficiency of cloning large DNA fragments using a lower copy number plasmid. *BioTechniques* 32: 992-998.
Feuk, et al., 2006. Structural variation in the human genome. Nature Rev 7: 85-97.
Fitzgerald et al., 1992. Rapid shotgun cloning utilizing the two base recognition endonuclease *CviJ I*. *Nuc Acid Res* 20: 3753-3762.
Fullwood et al., An oestrogen-receptor-alpha-bound human chromatin interactome, Nature 462:58-64, 2009.
Geier, et al., 1979. Recognition sequence of the dam methylase of *Escherichia coli*K12 and mode of cleavage of Dpn I endonuclease. *J Biol Chem* 254: 1408-1413.
Gonzalez, et al., 2005. The influence of CCL3L1 gene-containing segmental duplications on HIV-1/AIDS susceptibility. *Science* 307: 1434-1440.
Gray, et al., 2000. Genome changes and gene expression in human solid tumors. *Carcinogenesis* 21: 443-452.
Grindley, et al., 1980. Genetic and DNA sequence analysis of the kanamycin resistance transposon Tn903. *Proc Natl Acad Sci* (USA) 77: 7176-7180.
Hamelin, et al., 1990. Gel and buffer effects on the migration of DNA molecules in agarose. *Appl Theor Electrophor* I: 225-231 (not available).
Hampton et al., Long-range massively parallel mate pair sequencing detects distinct mutations and similar patterns of structural mutability in two breast cancer cell lines, Cancer Genet. 204:447-457, 2011.

Hattman, et al., 1978. Sequence specificity of the P1 modification methylase (M.Eco P1) and the DNA methylase (M. Eco dam) controlled by the *Escherichia coli* dam gene. *J Mol Biol* 126: 367-380.
Havlak, et al., 2004. The atlas genome assembly system. Genome Res 14: 721-732.
Hayashi et al., 1986. Regulation of inter- and intermolecular ligation with T4 DNA ligase in the presence of polyethylene glycol. *Nuc Acids Res* 14: 7617-7630.
Hearst and Stockmayer, Sedimentation constants of broken chains and wormlike coils, J Chem Phys 37:1425-1433, 1962.
Heffron et al., 1978. In vitro mutagenesis of a circular DNA molecule by using synthetic restriction sites. *Proc Natl Acad Sci* (USA) 74: 6012-6016.
Heiskanen, et al., 2000. Detection of gene amplification by genomic hybridization to cDNA microarrays. *Cancer Res* 60: 799-802.
Hilmer et al., Comprehensive long-span paired-end-tag mapping reveals characteristic patterns of structural variations in epithelial cancer genomes, Genome Res 21:665-675, 2011.
Holzman, et al., 1990. The genetics of schizophrenia: A review. *Pyschol Sci* 1: 179-286.
Huang, et al., 2004. Whole genome DNA copy number changes by high density oligonucleotides arrays. *Hum Genomics* 1: 287-299.
Huang, et al., 2006. Application of a superword array in genome assembly. *Nuc Acids Res* 34: 201-205.
Huang, et al., 2003. PCAP: A whole-genome assembly program. *Genome Res* 13: 2164-2170.
Inazawa, et al., 2004. Comparative genomic hybridization (CGH)-arrays pave the way for identification of novel cancer-related genes. *Cancer Sci* 95: 559-563.
Jacobson and Stockmayer, J Chem Phys 18:1600-1606, 1950 (not available).
Jaffe, et al., 2003. Whole-genome sequence assembly for mammalian genomes: ARACHNE 2. *Genome Res* 13: 91-96.
Kan, et al., 1979. The nucleotide sequence recognized by the *Escherichia coil* K12 restriction and modification enzymes. *J Mol Biol* 130: 191-209.
Kivioja et al., Counting absolute number of molecules using unique molecular identifiers, Nature Methods 9:72-76, 2012.
Korbel et al., 2007. Paired-end mapping reveals extensive structure variation in the Human genome. *Science* 318: 420-426.
Kozdroj, et al., 2001. Structural diversity of microorganisms in chemically perturbed soil assessed by molecular and cytochemical approaches. *J Microl Meth* 43: 187-212.
Lucito, et al., 2003. Representational oligonucleotide microarray analysis: A high-resolution method to detect genome copy number variation. *Genome Res* 13: 2291-2305.
MacKay, TFC, 2001. Quantitative trait loci in *Drosophila*. *Nat Rev Genet* 2:11-20.
Mahairas, et al., 1999. Sequence-tagged connectors: A sequence approach to mapping and scanning the human genome. *Proc Natl Acad Sci* (USA) 96: 9739-9744.
Mardis, 2008. Next-generation DNA sequencing methods. *Annu Rev Genomics Hum Genet* 9: 387-402.
Margulies, et al., 2005. Genome sequencing in microfabricated high-density picrolitre reactors. *Nature* 437: 376-380.
Matsumura, et al., 2003. Gene expression analysis of plant host-pathogen interactions by SuperSAGE. *Proc Natl Acad Sci* (USA) 100: 15718-15723.
May, et al., 1975. Analysis of bacteriophage deoxyribonucleic acid sequences methylated by host- and R-factor-controlled enzymes. *J Bacteriology* 123: 768-770.
McClelland, et al., 1994. Effect of site-specific modification on restriction endonucleases and DNA modification methyltransferases. *Nuc Acids Res* 22: 3640-3659.
McPherson (ed.), Directed Mutagenesis—A Practical Approach, Oxford University Press, New York, 1991 Book—Not Provided.
Melgar, et al., 1968. Deoxyribonucleic acid nucleases: II. The effect of metals on the mechanism of action of deoxyribonuclease 1. *J Biol Chem* 243: 4409-4416.
Morozova, et al., 2008. Applications of the next-generation sequencing technologies in functional genomics. *Genomics* 92: 255-262.

(56) References Cited

OTHER PUBLICATIONS

Mullikin, et al., 2003. The PHUSION assembler. *Genome Res* 13: 81-90.
Myers et al, 2000. A whole-genome assembly of *Drosophila*. Science 287: 2196-21204.
Ng et al., Gene identification signature (GIS) analysis for transcriptome characterization and genome annotation, Nature Methods 2:105-111, 2005.
Owen, et al., 1996. Modem molecular genetic approaches to complex traits: Implications for psychiatric disorders. *Mol Psychiatry* 1: 21-26.
Patterson,et al., 2009. Combinatorics and next-generation sequencing. *Nature Biotechnology* 27:826-827.
Pevzner, et al., 2001. Fragment assembly with double-barreled data. *Bioinformatics* 17 Suppl 1: S225-S233.
Pheiffer, et al., 1983. Polymer-stimulated ligation: Enhanced blunt- or cohesive-end ligation of DNA or deoxyribooligonucleotides by T4 DNA ligase in polymer solutions. *Nuc Acids Res* 11: 7853-7871.
Pinkel, et al., 2005. Array comparative genomic hybridization and its application in cancer. *Nat Genet* Suppl 37: S11-S17.
Pinkel, et al., 1998. High resolution analysis of DNA copy number variation using comparative genomic hybridization to microarrays. *Nat Genet* 20: 207-211.
Pollack, et al., 2002. Microarray analysis reveals a major direct role of DNA copy number alternation in the transcriptional program of human breast tumors. *Proc Natl Acad Sci* (USA) 99: 12963-12968.
Pollack, et al., 1999. Genome-wide analysis of DNA copy-number changes using cDNA microarrays. *Nat Genet* 23: 41-46.
Pop, et al., 2004. Comparative genome assembly. Briefings in Bioinformatics 5: 237-248.
Redon, et al., 2006. Global variation in copy number in the human genome. *Nature* 444: 444-454.
Rickwood and Hames (eds.), Gel Electrophoresis of Nucleic Acids—A Practical Approach, Oxford University Press, New York, 1990 Book—Not Provided.
Rommens et al., Identification of the cystic fibrosis gene: chromosome walking and jumping, Science 245:1059-1065, 1989.
Rouillard, et al., 2001. Virtual genome scan: A tool for restriction landmark-based scanning of the human genome. *Genome Res* 11: 1453-1459.
Saha, et al., 2002. Using the transcriptome to annotate the genome. *Nat Biotech* 19: 508-512. Salzberg SL and Yorke JA, 2005. Beware of mis-assembled genomes. Bioinformatics 21: 43204321.
Sambrook et al., Molecular Cloning: A Laboratory Manual $2^{nd}$ Ed, CSH Press, New York, 1989 Book—Not Provided.
Sanger, et al., 1977. DNA sequencing with chain terminating inhibitors. *Proc Natl Acad Sci* (USA) 74: 5463-5467.
Schloter, et al., 2000. Ecology and evolution of bacterial microdiversity. *FEMS Micobiol Rev* 21: 647-660.
Shriefer et al., 1990. Low pressure DNA shearing: A method for random DNA sequence analysis. *Nuc Acids Res* 18: 7455.
Shendure et al., The expanding scope of DNA sequencing, Nature Biotechnology 30:1084-1094, 2012.
Sistla, et al., 2004. S-adenosyl-L-methionine-dependent restriction enzymes. *Crit Rev Biochem Mol Biol* 39:1-19.
Snijders, et al., 2001. Assembly of microarrays for genome-wide measurement of DNA copy numbers. *Nat Genet* 29: 263-264.
Tao, et al., 1998. Cloning and stable maintenance of DNA fragments over 300 kb in *Escherichia coli* with conventional plasmid-based vectors. *Nuc Acids Res* 21: 4901-4909.
Tuzun, et al., 2005. Fine-scale structural variation of the human genome. *Nat Genet* 37: 727-732.
Velculescu, et al., 1995. Serial analysis of gene expression. *Science* 270: 484-487.
Volik, et al., 2006. Decoding the fine-scale structure of a breast cancer genome and transcriptome. *Genome Res* 16: 394-404.
Wang, et al., 1966. On the probability of ring closure of lambda DNA. *J Mol Biol* 19: 469-482.
Warren, et al., 2006. Physical map-assisted whole-genome shotgun sequence assemblies. *Genome Res* 16: 768-775.
Wei, et al., 2004. 5' long serial analysis of gene expression (LongSAGE) and 3' LongSAGE for transcriptome characterization and genome annotation. *Proc Natl Acad Sci* (USA) 101: 11701-11706
Weinstock, et al., 2006. Insights into social insects from the genome of the honeybee *Apis mellifera*. Nature 443: 931-949.
Wetzel et al., Assessing the benefits of using mate-pairs to resolve repeats in de novo short-read prokaryotic assemblies, BMC Bioinformatics 12:95, 2011.
Williams et al., Paired-end sequencing of Fosmid libraries by Illumina, Genome Res 22:224-2249, 2012.
Wimmer, et al., 2002. Combined restriction landmark genomic scanning and virtual genome scans identify a novel human homeobox gene, ALX3, that is hypermethylated in neuroblastoma. *Genes Chromosomes & Cancer* 33: 285-294.
Zhang, et al., 2000. A greedy algorithm for aligning DNA sequencing. I *Computational Biol* 7: 203-214.
Zhao, S., 2000. Human BAC ends. Nuc Acids Res 28: 129-132.
Zimmerman, et al., 1983. Macromolecular crowding allows blunt-end ligation by DNA ligases from rat liver or *Escherichia coli*. *Proc Natl Acad Sci* (USA) 80: 5852-5856.

TRUE MATE-PAIR SEQUENCE tggact*CCACTGTGTAAGGAGAACGA*TCTACATGGTTGTAGGCATTGTGCCGC
GCGATGCGGGCAACATCATTATTGATGATGACGATATCAGTCTGCTGCCTCTG
CATGCACGCGCGCCGCGGTATCGGGGTACATCCGCTTGGCCAAGGCGGATG
TACCCTCGACCATTCCCGTCCATCGATTTTCGCACCACAGCGGAGCAAGCAGC
GTCGGGCGACGGGCGCTGGCGGAAATGCGGTGGTAGATCACTTCCGGTGGCGT
ATGGCGAATCATTTCTCCGGCAGTGAGCGTGTAATCCTCCAGTTCAATACCGT
TCAAACGCCC*ATCGTTCTCCTTACAACATTGG*tctgga (SEQ ID NO:7)

Paired Molecular identity tags (MITs)
MIT A: tggact
MIT B: tctgga  } Separation of inserts on genome: 9,280 bp

FIG. 10A

CHIMERIC SEQUENCE tggact*CCACTGTGTAAGGAGAACGA*TCATACGTGAATTCGACGGCGGCGATT
AAAGCGTTCGTTGGACGCCGGTACATCCGCCTTGGCCAAGGCGGATGTACCCG
CTGCTTCCCGGAAAGAAAAGTTAGCCGGAAAAAACCAGATCGGGATCATTGGC
TATGCTTCGCTTTTTTCGTTCTGTTTTTTCCATTTTCACGTATATACATGAAG
AGAAGTAACAAAAAGGGGGAGAGTTTGATGGCTTACTTCGGCTCGAAAGGATG
GCTCGTCCAACAATTAAAAGAGGCGGGAATTCGTTGGCATCCTATGGAAAGGA
AAAAAATTGAAACTATAAAAGCGGCGATTTTATA*ATCGTTCTCCTTACACATT
Gg*acttcg (SEQ ID NO:8)

Non-Paired Molecular identity tags(MITs)
MIT A: tggact
MIT C: acttcg  } Separation of inserts on genome: 693,782 bp

FIG. 10B

MOLECULAR IDENTITY TAGS AND USES THEREOF IN IDENTIFYING INTERMOLECULAR LIGATION PRODUCTS

CROSS-REFERENCE TO RELATED APPLICATIONS

This application claims priority under 35 USC § 119(e) to U.S. Provisional Patent Application 61/956,050 filed May 31, 2013, the entirety of which is incorporated herein by reference.

FIELD OF THE INVENTION

The invention is directed to tools and methods for identifying intermolecular nucleic acid ligation products, for use in generating and analyzing mate-pair libraries and other uses.

BACKGROUND

Precise intramolecular ligation of nucleic acid fragments has many important applications in genomics. In the method described by Collins and Weissman (*Proc Natl Acad Sci USA* 81:6812-6816, 1984), intramolecular ligation (circularization) of long DNA fragments is employed to juxtapose distal co-linear DNA segments to produce so termed "genomic jumping libraries" to study gene structure at a chromosomal scale (Collins et al., *Science* 235:1046-1049, 1987). Despite several technical challenges with this method, such as difficulties in producing large, circular DNA molecules and artifacts arising from the generation of intermolecularly ligated DNA species, genomic jumping libraries have contributed to important gene discoveries. One of these discoveries includes the identification of the cystic fibrosis locus (Rommens et al., *Science* 245:1059-1065, 1989). Building on the approach of Collins and Weissman, the method of Ng et al. (*Nature Methods* 2:105-111, 2005) circularizes individual cDNAs to link 5'- and 3'-derived "serial analysis of gene expression" (SAGE) tags to produce "paired-end ditags" (PETs) to demarcate gene boundaries.

"Next generation" massively parallel sequencers with their capacity to generate tens of millions of individual sequence reads per instrument run have changed the field of genomics and the related disciplines. For review, see Mardis, *Annu Rev Genomics Hum Genet* 9:387-402, 2008; and Shendure and Aiden, *Nature Biotechnology* 30:1084-1094, 2012. Accurate intramolecular ligation is integral to mate-pair or paired-end read technologies for use on the new DNA sequencing platforms to identify human genomic variations and to produce comprehensive scaffolds for de novo genomic assembly. See: Edgren et al., *Genome Biol* 12:R6, 2011; Hampton et al., *Cancer Biol* 204:447-457, 2011; Hillmer et al., *Genome Res* 21:665-675, 2011; Hampton et al., *Cancer Genet* 204:447-457, 2011; and Wetzel et al., *BMC Bioinformatics* 12:95, 2011. Despite the potential usefulness of mate-pair sequencing, the method as it is currently practiced is hampered by difficulties in producing circular nucleic acid molecules by intramolecular ligation. Intramolecular ligation is a critical step in the construction of mate-pair libraries, especially those of long and useful separation distances. Competing intermolecular ligation of DNA fragments during mate-pair library construction results in unwanted juxtaposition of random DNA fragments, creating so-called "chimeric" mate-pair reads. The chimeric mate-pair reads constitute unacceptable background for the identification of structural variations and for use in de novo sequence assembly.

The theoretical basis of ligating linear DNA molecules in solution has been described. Jacobson and Stockmayer (*J Chem Phys* 18:1600-1606, 1950) modeled DNA as a series of rigid segments of length b, joined by freely movable joints, and of total contour length 1. For intramolecular ligation to take place, the effective concentration, j, of one end of a long DNA molecule in neighborhood of the other end can be represented by the equation:

$$j=(3/\pi lb)^{3/2} \text{ ends per ml}$$

The value for b has been estimated by Hearst and Stockmayer (*J Chem Phys* 37:1425-1433, 1962) to be $7.2\times10^{-2}$ micrometer from sedimentation data, leading to the simplification:

$$j=63.4/(kb)^{1/2} \text{ µg/ml},$$

where kb is the length DNA fragment in kilobase.

These theoretical bases are consistent with experimental results of Collins and Weisman (*Proc Natl Acad Sci USA* 81:6812-6816, 1984). When a ligation reaction is carried out at a DNA concentration i, which is less than j, the formation of circles by intermolecular ligation is favored. However, when i is greater than j, intermolecular ligation of DNA fragments yielding chimeric DNA molecules is favored. Accordingly, at any given DNA concentration, i, the fraction of circles formed can be predicted by the equation:

$$\% \text{ circles}=j/(i+1)\times100$$

Ligation of DNA is therefore highly dependent on the concentration of DNA ends.

The above theoretical considerations provide the underpinning for the observed difficulties in producing efficient mate-pair libraries, especially of long separation distance. A necessary trade-off to favor intramolecular ligation over intermolecular ligation during mate-pair library construction is that the ligation reaction must be performed at ever increasing dilution as the DNA fragment length increases with a consequent loss of efficiency. Most critically, even when carried out under theoretically optimal conditions favoring intramolecular ligation, there is still a significant background of intermolecular ligation events that is unacceptable for stringent applications such as the generation of scaffolds for de novo assembly of large complex genomes or for the identification of rearrangements in cancer genomes.

Two general methods for constructing mate-pair libraries are presently in use. See Korbel et al., (*Science* 318:420-426, 2007) and Lok (U.S. Pat. Nos. 7,932,029 and 8,329,400). In the method of Korbel et al., a common biotin-labeled adapter sequence is ligated to the terminal ends of target DNA. The adapter-ligated DNA is then circularized to juxtapose the terminal ends. The resulting circularized molecule is then randomly fragmented, and the newly jointed junction fragments are recovered by biotin affinity chromatography. The recovered fragments are then ligated to sequencing adapters to generate a mate-pair library ready for amplification and sequencing. In the method of Lok, a target DNA fragment is ligated to a short DNA backbone under dilute conditions to create a circular molecule. The bulk of the target DNA insert is then digested with enzymes to create a linear DNA molecule comprising short terminal fragments of the target DNA insert attached to the DNA backbone. This linear DNA fragment is then re-circularized by a second ligation reaction, juxtaposing the terminal regions of the target DNA insert to create the mate-pair library. During the critical circularization steps in both methods, a significant proportion of the ligation products are unwanted intermolecular, chimeric ligation products. The intermolecular products lead to artifactual mate-pair sequence reads, which greatly compromise the library and subsequent data analysis.

Methods and tools for reducing the effects of intermolecular, chimeric ligation products in the generation and analysis of mate-pair libraries, for example, are needed.

SUMMARY OF THE INVENTION

The present invention uses multiple pairs of distinguishable molecular identity tags to mark the terminal regions of individual target nucleic acids and thereby enable identifying intermolecular ligation products and distinguishing intermolecular ligation products from intramolecular ligation products. The terminal regions of each target nucleic acid are marked with a pair of molecular identity tags such that a first terminal region of the target nucleic acid is marked with a first member of the pair and a second terminal region is marked with a second member of the pair. This process results in a pool of marked target nucleic acids in which at least some, and preferably most, of the target nucleic acids are marked with different pairs of molecular identity tags. Ligating the marked target nucleic acids will likely result in both intramolecularly ligated circular species and intermolecularly ligated chimeric species. The intermolecular ligated chimeric species are created by intermolecular ligation between two or more different marked nucleic acids. Sequencing the molecular identity tags juxtaposed in the ligation reaction can indicate whether a particular nucleic acid is an intramolecularly ligated species or an intermolecularly ligated species. The presence of juxtaposed paired molecular identity tags indicates a probable intramolecularly ligated species. The presence of juxtaposed unpaired molecular identity tags indicates a probable intermolecularly ligated species.

In a preferred embodiment, the present invention is used to create improved mate-pair libraries where chimeric mate-paired reads resulting from intermolecular ligation between nucleic acid fragments can be identified and eliminated in silico. The present invention can be incorporated into any method capable of generating mate-pair libraries, including the method Korbel et al., (*Science* 318:420-426, 2007), the method of Lok (U.S. Pat. Nos. 7,932,029 and 8,329,400), the method of Williams et al. (*Genome Res* 22:224-2249, 2012), variations thereof, and others. The present invention for improved mate-pair library construction is useful for accurate identification of nucleic acid structural variations such as insertions, deletions, inversions, and translocations; for the generation of scaffolds for de novo sequence assembly; and the like.

Accordingly, the invention provides methods of marking target nucleic acids for distinguishing intermolecular products thereof. One method comprises a step of marking linear target nucleic acids with multiple, mutually distinguishable pairs of molecular identity tags to yield marked target nucleic acids. The marking comprises marking terminal regions of each linear target nucleic acid with one of the pairs of molecular identity tags, wherein a first terminal region of each target nucleic acid is marked with a first member of the one of the pairs and a second terminal region of each target nucleic acid is marked with a second member of the one of the pairs. The method further comprises a step of joining terminal ends of the marked target nucleic acids or products of the marked target nucleic acids to yield marked nucleic acid products. Each marked nucleic acid product comprises two of the molecular identity tags juxtaposed across the joined terminal ends. Any marked nucleic acid product comprising juxtaposed unpaired molecular identity tags constitutes an intermolecular nucleic acid product.

The marked nucleic acid products in some versions may include one or more marked nucleic acid products comprising only juxtaposed paired molecular identity tags as well as one or more marked nucleic acid products comprising juxtaposed unpaired molecular identity tags. In such versions, the one or more marked nucleic acid products comprising only juxtaposed paired molecular identity tags (or products thereof) may be parsed from the one or more marked nucleic acid products comprising juxtaposed unpaired molecular identity tags (or products thereof). Products of the marked nucleic acid products that may be parsed include digestions of the marked nucleic acid products and amplicons of the marked nucleic acid products, among others. In preferred versions, the parsing comprises sequencing the marked nucleic acid products or products thereof. The sequences comprising only juxtaposed paired molecular identity tags and the sequences comprising juxtaposed unpaired molecular identity tags may then be identified, and the sequences comprising juxtaposed unpaired molecular identity tags may be removed from the sequences comprising only juxtaposed paired molecular identity tags.

In some versions, the joining yields circularized, marked nucleic acids. Such versions may further comprise linearizing the circularized, marked nucleic acids to yield one or more linearized, marked nucleic acids comprising only juxtaposed paired molecular identity tags and one or more linearized, marked nucleic acids comprising juxtaposed unpaired molecular identity tags. In such versions, the parsing comprises parsing the one or more linearized, marked nucleic acids comprising only juxtaposed paired molecular identity tags from the one or more linearized, marked nucleic acids comprising juxtaposed unpaired molecular identity tags. The linearizing is preferably selected from the group consisting of fragmenting (i.e., digesting, shearing, sonicating, etc.) the circularized, marked nucleic acids and amplifying linear portions of the circularized, marked nucleic acids.

In some versions, each pair of molecular identity tags is physically linked. The molecular identity tags may be physically linked by a short intervening adaptor, linker, or coupler sequence (see FIGS. 4 and 5). Marking the linear target nucleic acids in such versions comprises marking the terminal regions of each linear target nucleic acid with one of the physically linked pairs of molecular identity tags to yield "end-coupled," marked target nucleic acids. A portion of the original target nucleic acid may then be excised from each of the end-coupled, marked target nucleic acids to yield sequence-excised, marked target nucleic acids. "Insert tags" from the original target nucleic acid preferably remain in the sequence-excised, marked target nucleic acids. The sequence-excised, marked target nucleic acids may then be circularized to yield the marked nucleic acid products.

In some versions, marking the target nucleic acids comprises marking the terminal regions of the linear target nucleic acids with non-physically linked pairs of molecular identity tags. One method of marking the terminal regions of the linear target nucleic acids with non-physically linked pairs of molecular identity tags comprises dividing the linear target nucleic acids into first aliquots, terminally attaching a different partial molecular identity tag to the divided target nucleic acids in each first aliquot to generate partially marked target nucleic acids, pooling the partially marked target nucleic acids, dividing the pooled partially marked target nucleic acids into second aliquots, and terminally attaching a different partial molecular identity tag to the divided partially marked target nucleic acids in each second aliquot to generate the marked target nucleic acids.

In some versions, joining terminal ends of the marked target nucleic acids or products of the marked target nucleic acids to yield marked nucleic acid products includes inserting a nucleic acid comprising a junction code between the joined terminal ends of the marked target nucleic acids or products of the marked target nucleic acids.

The invention also provides reagents for marking target nucleic acids for distinguishing intermolecular products thereof. One set of reagents comprises a plurality of nucleic acids. Each nucleic acid comprises at least a first nucleic acid strand. The first nucleic acid strand on each nucleic acid comprises a first molecular identity tag, a first primer-binding site, a second molecular identity tag, and a reverse complement of a second primer-binding site. The first molecular identity tag is preferably located on the first nucleic acid strand in a 5' position with respect to the first primer-binding site. The second molecular identity tag preferably is located on the first nucleic acid strand in a 3' position with respect to the reverse complement of the second primer-binding site. In addition, the first molecular identity tag and the first primer-binding site are preferably located on the first nucleic acid strand in a 5' position with respect to the second molecular identity tag and the reverse complement of the second primer-binding site. It is preferred that the first primer-binding sites in the nucleic acids are substantially identical with each other, that the reverse complements of the second primer-binding sites in the nucleic acids are substantially identical with each other, that the first molecular identity tags in a set of at least two the nucleic acids are distinguishable from each other, and that the second molecular identity tags in the set of the nucleic acids are distinguishable from each other.

In some versions, the nucleic acids comprise multiple copies of each nucleic acid in the set of nucleic acids having distinguishable first molecular identity tags and second molecular identity tags, such that the plurality of nucleic acids comprises at least two copies of each nucleic acid in the set.

In some versions, each of the nucleic acids is a linear nucleic acid including a first terminus and a second terminus. In such versions, the first molecular identity tag is preferably located between the first terminus and the second molecular identity tag, and the second molecular identity tag is preferably located between the second terminus and the first molecular identity tag.

In some versions in which each of the nucleic acids is a linear nucleic acid including a first terminus and a second terminus, each of the first nucleic acid strands comprises from 0 to about 90 bases between a 5' end of the first molecular identity tag and the first terminus, and further comprises from 0 to about 90 bases between the second terminus and a 3' end of the second molecular identity tag.

In some versions in which each of the nucleic acids is a linear nucleic acid including a first terminus and a second terminus, each of the first nucleic acid strands comprises from 3 to about 150 bases between a 5' end of the first primer-binding site and the first terminus, and further comprises from 3 to about 150 bases between the second terminus and a 3' end of the reverse complement of the second primer-binding site.

In some versions, each of the first nucleic acid strands comprises of from about 30 bases to about 10 kilobases or more.

In some versions, the first molecular identity tags and the reverse complements of the second molecular identity tags each independently have a length of from about 2 to about 30 bases or more.

In some versions, each nucleic acid includes a second nucleic acid strand that comprises a reverse complement of the first molecular identity tag, a reverse complement of the first primer-binding site, the second primer-binding site, and a reverse complement of the second molecular identity tag.

In some versions, the set of nucleic acids comprising distinguishable first molecular identity tags and distinguishable second molecular identity tags includes at least 10 of the nucleic acids.

The objects and advantages of the invention will appear more fully from the following detailed description of the preferred embodiment of the invention made in conjunction with the accompanying drawings.

BRIEF DESCRIPTION OF THE DRAWINGS

FIG. 10A depicts an exemplary sequence read (SEQ ID NO:7) of a true mate-pair sequence. Underlined, lowercase letters indicate molecular identity tag sequences. Italicized, uppercase letters indicate insertion adapter sequences. Non-underlined, non-italicized uppercase letters indicate target nucleic acid sequence (E. coli). Underlined, uppercase letters indicate a junction code sequence.

FIG. 10B depicts an exemplary sequence read (SEQ ID NO:8) of a chimeric sequence. Underlined, lowercase letters indicate molecular identity tag sequences. Italicized, uppercase letters indicate insertion adapter sequences. Non-underlined, non-italicized uppercase letters indicate target nucleic acid sequence (E. coli). Underlined, uppercase letters indicate a junction code sequence.

DETAILED DESCRIPTION OF THE INVENTION

Figure 1:
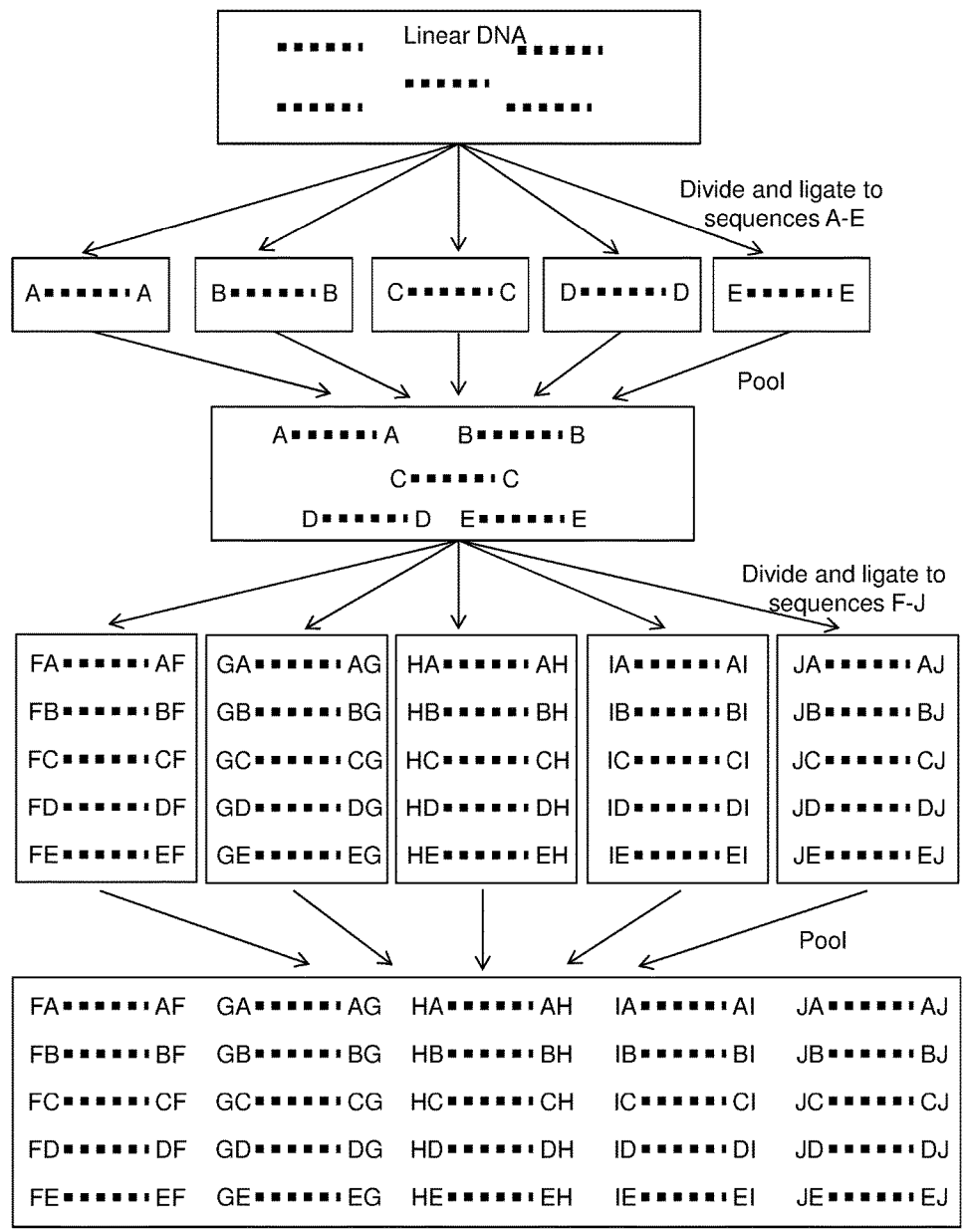
FIG. 1 is a flowchart showing an exemplary method of marking nucleic acids by attaching non-physically linked molecular identity tag segments (letters A-J) to target DNA (dotted lines) using successive aliquotting, attachment, and pooling.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

Molecular Identity Tags.

The molecular identity tags of the present invention are nucleic acids, or portions thereof, having known sequences that are distinguishable and recognizable to a user in a given stretch of nucleic acid. The molecular identity tags preferably comprise at least two bases and may be as long as is practical for the particular technique in which it is employed. As an example, the molecular identity tags may comprise from 2 to about 100 bases, from 2 to about 50 bases, from 2 to about 40 bases, from 2 to about 30 bases, from 2 to about 25 bases, from 2 to about 20 bases, from 2 to about 15 bases, from 2 to about 10 bases, or from 2 to about 8 bases, or from about 4 to about 8 bases. In an exemplary version of the invention, the molecular identity tags comprise 6 bases.

As described herein, the molecular identity tags are preferably employed as a group that includes multiple pairs. The molecular identity tags in a given pair may be physically linked, for example, by being included on the same nucleic acid, or may be physically separate (non-physically linked). Accordingly, physically linked molecular identity tags are paired by virtue of their physical linkage. Non-physically linked molecular identity tags may be paired by virtue of the method in generating them (see, e.g, FIG. 1), by encoding them as pairs in a software analysis program, or other ways.

Each molecular identity tag in a given pair is distinguishable from the molecular identity tags of other pairs. Molecular identity tags may be distinguishable by being non-identical. The molecular identity tags within a group may have different lengths. However, as the molecular identity tags are typically embedded among other bases in a nucleic acid sequence, the molecular identity tags are preferably distinguishable by a characteristic other than the length of the sequence, such as by having a non-identical sequence over a certain number of bases (e.g., 2, 3, 4, 5, 6, 7, 8, 9, 10, 15, 20, 25, etc.). The molecular identity tags in a given pair may be distinguishable from each other but need not be. Thus, the molecular identity tags in each pair of a given group may be identical or non-identical. In addition, some pairs in a given group may comprise identical molecular identity tags and other pairs in the same given group may comprise non-identical molecular identity tags. The false positive rate of identifying a particular nucleic acid (or sequence thereof) as an intramolecular product is reduced when the pairs comprise non-identical molecular identity tags as compared to when the pairs comprise identical molecular identity tags.

A group of molecular identity tags may comprise as few as two pairs of molecular identity tags and up to as many pairs of molecular identity tags as is practical for a given purpose. For example, a group of molecular identity tags may include from about 2 to about 10,000 or more, from about 2 to about 1,000, from about 2 to about 500, from about 2 to about 100, from about 2 to about 50, from about 5 to about 10,000 or more, from about 5 to about 1,000, from about 5 to about 500, from about 5 to about 100, from about 5 to about 50, from about 10 to about 10,000, from about 10 to about 1,000, from about 10 to about 500, from about 10 to about 100, from about 10 to about 50, from about 20 to about 10,000, from about 20 to about 1,000, from about 20 to about 500, from about 20 to about 100, or from about 20 to about 50 pairs of molecular identity tags. The false positive rate of identifying a particular nucleic acid (or sequence thereof) as an intramolecular product depends on the number of pairs of molecular identity tags used. False positive assignment of intramolecular status arises principally through the chance intermolecular joining of two target nucleic acids comprising the same pair of molecular identity tags. For example, under conditions where intramolecular and intermolecular ligation of a population of DNA fragments occurs in equal frequency (50%), the use of 10 unique pairs of molecular identity tags in library construction would have a false positive rate for calling intramolecular ligation events of 1 in 10 (10%), which is a 5-fold improvement in the false positive rate over the base frequency. The use of 100 unique pairs of molecular identity tags in library construction would have a false positive rate for calling intramolecular ligation events of 1 in 100 (1%), which is a 50-fold improvement in the false positive rate over the base frequency. Thus, the number of molecular identity tag pairs used in library construction is inversely proportional to the false positive rate. The present invention allows the end-user to balance the tradeoff between an acceptable false positive rate and the logistical and cost constraints in library construction to suit experimental needs. It should be noted that the false negative rate with the present invention, where a true intramolecular ligation product is incorrectly classified as an intermolecular ligation product, is essentially zero. Use of non-identical The length of the bases in the molecular identity tags within a group determines the number of distinguishable sequences in the group and, hence, the number of pairs of distinguishable sequences in a group. Lengths of 2-10 bases are typically sufficient for most purposes, as sequences only 8 bases in length, for example, provide 65,536 possible sequence combinations.

Nucleic Acid Couplers.

Physically linked paired molecular identity tags may be provided in any of a number of versions. The physically linked paired molecular identity tags are preferably provided on nucleic acid couplers. The term "coupler" refers to any nucleic acid capable of joining two ends of a linear nucleic acid to form a circular nucleic acid. The term refers to nucleic acids that include molecular identity tags as well as those that do not. The couplers of the invention are preferably comprised of nucleic acids such as DNA or RNA, with DNA being preferred. The couplers of the invention may include elements for propagating in a microbial host, such as a replication origin, a selection marker, partitioning elements, or other elements well-known in the art for facilitating propagation in a microbial host. Alternatively, the couplers of the invention may be devoid of elements for propagating in a microbial host. Couplers capable of propagating in a microbial host are referred to herein as "vectors." Couplers incapable of propagating in a microbial host are referred to herein as "nucleic acid backbones."

Figure 5:
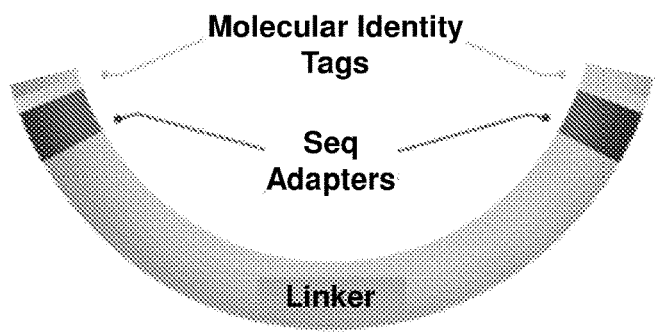
FIG. 5 is a schema depicting a coupler of the present invention comprising physically linked molecular identity tags.

In some versions of the invention, each coupler comprises a pair of molecular identity tags and a nucleic acid linker disposed between each molecular identity tag. To facilitate sequencing the molecular identity tags and any target nucleic acid attached thereto, the couplers also preferably comprise sequence adapters that include primer-binding sites. The structure of an exemplary coupler is shown in FIG. 5.

The couplers may be provided in any of a variety of forms, such as a linear, single-stranded form; a linear, double-stranded form; a circular, single-stranded form; a circular, double-stranded form; or mixtures thereof. The form used to ligate to target nucleic acids in the methods described herein is the linear, double-stranded form. Therefore, couplers provided in the linear, single-stranded form; the circular, single-stranded form; or the circular, double-stranded form are first converted to the linear, double-stranded form before ligating to target nucleic acids. The single-stranded forms can be converted to the double-stranded forms by complementary strand synthesis. The circular forms can be converted to the linear forms by PCR amplification, restriction digestion, or other methods.

Each nucleic acid strand preferably comprises at least a first molecular identity tag and a second molecular identity tag. The first molecular identity tag and the second molecular identity tag are preferably separated by a linker. The first molecular identity tag is preferably disposed in a 5' position with respect to the linker, and the second molecular identity tag is preferably disposed in a 3' position with respect to the linker. If the nucleic acid strand is in linear form the linear nucleic acid thus preferably comprises, from the 5' end to the 3' end of the molecule, the first molecular identity tag, the linker, and the second molecular identity tag.

If the nucleic acid strand is in circular form, a separation site taking the form of one or more known restriction sites is disposed between the first molecular identity tag and the reverse complement of the second molecular identity tag. Thus, converting the circular nucleic acid to a linear nucleic acid at the separation site yields a linear nucleic acid comprising, from the 5' end to the 3' end of the molecule, the first molecular identity tag, the linker and the second molecular identity tag.

When the coupler is in linear form, the coupler preferably comprises from 0 to about 400 bases, from 0 to about 300 bases, from 0 to about 200 bases, from 0 to about 100 bases, from 0 to about 90 bases, from 0 to about 80 bases, from 0 to about 70 bases, from 0 to about 60 bases, from 0 to about 50 bases, from 0 to about 40 bases, from 0 to about 30 bases, from 0 to about 20 bases, from 0 to about 10 bases, from 0 to about 5 bases, or 0 bases between a 5' end of the first molecular identity tag and the 5' terminus of the coupler.

When the coupler is in linear form, the coupler preferably comprises from 0 to about 400 bases, from 0 to about 300 bases, from 0 to about 200 bases, from 0 to about 100 bases, from 0 to about 90 bases, from 0 to about 80 bases, from 0 to about 70 bases, from 0 to about 60 bases, from 0 to about 50 bases, from 0 to about 40 bases, from 0 to about 30 bases, from 0 to about 20 bases, from 0 to about 10 bases, from 0 to about 5 bases, or 0 bases between a 3' end of the second molecular identity tag and the 3' terminus of the coupler.

In addition to the first molecular identity tag and the second molecular identity tag, each nucleic acid strand may comprise a first primer-binding site and a reverse complement of a second-primer binding sequence. The first primer-binding site is preferably disposed between the first molecular identity tag and the linker, and the reverse complement of the second primer-binding site is preferably disposed between the second molecular identity tag and the linker. If the nucleic acid strand is in linear form the linear nucleic acid thus preferably comprises, from the 5' end to the 3' end of the molecule, the first molecular identity tag, the first primer-binding site, the linker, the reverse complement of the second primer-binding site, and the second molecular identity tag. If the nucleic acid strand is in circular form, converting the circular nucleic acid to a linear nucleic acid at the separation site preferably yields a linear nucleic acid comprising, from the 5' end to the 3' end of the molecule, the first molecular identity tag, the first primer-binding site, the linker, the reverse complement of the second primer-binding site, and the second molecular identity tag.

When the coupler is in linear form, coupler preferably comprises from 0 to about 400 bases, from 0 to about 300 bases, from 0 to about 200 bases, from 0 to about 100 bases, from 0 to about 90 bases, from 0 to about 80 bases, from 0 to about 70 bases, from 0 to about 60 bases, from 0 to about 50 bases, from 0 to about 40 bases, from 0 to about 30 bases, from 0 to about 20 bases, from 0 to about 10 bases, from 0 to about 5 bases, or 2 bases between a 5' end of the first primer-binding site and the 5' terminus of the coupler.

When the coupler is in linear form, coupler preferably comprises from 0 to about 400 bases, from 0 to about 300 bases, from 0 to about 200 bases, from 0 to about 100 bases, from 0 to about 90 bases, from 0 to about 80 bases, from 0 to about 70 bases, from 0 to about 60 bases, from 0 to about 50 bases, from 0 to about 40 bases, from 0 to about 30 bases, from 0 to about 20 bases, from 0 to about 10 bases, from 0 to about 5 bases, or 2 bases between a 3' end of the reverse complement of the second molecular identity tag and the 3' terminus of the coupler.

The primer-binding sites on the couplers are configured to permit amplification and sequencing of any intervening sequences ultimately disposed between them in a direction opposite the linker, such as the molecular identity tags, target nucleic acid sequences (such as insert tags), and junction codes. See, e.g., FIG. 6. The sequences of the primer-binding sites are preferably known prior to use of the couplers. The primer-binding sites may comprise any length, such as from 2 to about 200 bases, from 2 to about 100 bases, from 2 to about 75 bases, from 2 to about 50 bases, from about 5 to about 200 bases, from about 5 to about 100 bases, from about 5 to about 75 bases, or from about 5 to about 50 bases. Lengths above these ranges are also acceptable.

In a preferred version of the couplers, the primer-binding sites comprise known sequencing adapters for use in one of the many so-called "next-generation" sequencing platforms. Examples of the next-generation sequencing platforms include the GENOME SEQUENCER FLX system (Roche Diagnostics, Indianapolis, Ind.; 454 Life Science Corp, Bradford, Conn.) (commonly refer as a "454-sequencer"), the SOLEXA GENOME ANALYZER (Illumina, San Diego, Calif.) (commonly referred to as "SOLEXA sequencer"), the ILLUMINA MISEQ and HISEQ systems (Illumina, Inc., San Diego, Calif.), the ION TORRENT ION PGM system (Life Technologies, Carlsbad, Calif.), and the SOLID sequencer (Applied Biosystems, Foster City, Calif.), among others. Suitable sequencing adapters include the SOLEXA "Adaptor-A" and "Adaptor-B" sequences (see U.S. Pat. No. 8,329,400), Roche Diagnostics' 454-Internal Adaptors (see U.S. Pat. No. 8,329,400), the "Adaptor-A" and "Adaptor-B" sequences from the Roche Diagnostics' 454-platform (see U.S. Pat. No. 8,329,400), sequences 5'-CCATCTCATCCCT-GCGTGTCTCCGACTCAG-3' (SEQ ID NO:1) and 5'-AT-CACCGACTGCCCATAGAGAGGAAAGCGGAGGCG-TAGTGG-3' (SEQ ID NO:2) for use with the ION TORRENT ION PGM sequencer, and sequences 5'-ACACTCTTTCCCTACACGACGCTCTTCCGATCT-3' (SEQ ID NO:3) and 5'-AGATCGGAAGAGCACACGTCT-3' (SEQ ID NO:4) for use with the ILLUMINA MISEQ and HISEQ sequencers.

The couplers are preferably devoid of common restriction enzyme sites found in genomic DNA. This enables digestion of insert target DNA in the process of generating mate pairs without digesting the couplers. As an example, the couplers provided in the examples described below are devoid of restriction sites for AluI, RsaI, HpyCH4V, AccII, HaeIII, and CviJI (PuGCPy).

The couplers are preferably provided and used as a group of couplers. The group of couplers preferably comprises multiple copies of each of several different species of coupler. The different species of coupler preferably differ at least with respect to the molecular identity tags comprised within, such that each species of coupler comprises molecular identity tags that are each distinguishable from the molecular identity tags on the other species of coupler. See, e.g., FIGS. 8A-8L, wherein each different species of coupler comprises a different pair of molecular identity tags (A-X).

As discussed above, the number of molecular identity tag pairs used in the methods described herein is inversely proportional to the false positive rate in identifying products of intermolecular ligation events. Thus, higher numbers of species within a group of couplers is beneficial for reducing false positive rates in identifying products of intermolecular ligation events. A group of couplers of the present invention may comprise as few as two species of couplers and up to as many species of couplers as is practical for a given purpose. For example, a group of couplers may include from about 2 to about 10,000, from about 2 to about 1,000, from about 2 to about 500, from about 2 to about 100, from about 2 to about 50, from about 5 to about 10,000, from about 5 to about 1,000, from about 5 to about 500, from about 5 to about 100, from about 5 to about 50, from about 10 to about 10,000, from about 10 to about 1,000, from about 10 to about 500, from about 10 to about 100, from about 10 to about 50, from about 20 to about 10,000, from about 20 to about 1,000, from about 20 to about 500, from about 20 to about 100, or from about 20 to about 50 species of couplers.

Generating groups of couplers with large numbers of species can be accomplished by degenerate oligonucleotide synthesis and sequencing. For example, distinguishable molecular identity tags can be synthesized as complex degenerate oligonucleotide sequences flanking an insert cloning site on a nucleic acid scaffold, such as a nucleic acid backbone or vector. The chemical synthesis of complex degenerate oligonucleotides is known in the art. The nucleic acid scaffolds containing the degenerate oligonucleotide sequences are diluted to a volume representing the desired number of distinguishable molecular identity tag pairs and are amplified by PCR. A small portion of the amplified nucleic acid scaffold is sequenced to generate a list of paired molecular identity tags. The remaining portion of the amplified scaffold may then be used as couplers for the construction of mate-pair libraries in the manner described herein. The preparation of a group of coupler species comprising 10,000 pairs of molecular identity tags can be easily produced and yield mate-pair libraries with a 0% false-negative rate and a potential false-positive rate of less than 0.01% ($\frac{1}{10,000}$).

Although not required, the elements of the couplers in a group other than the molecular identity tags may have sequences that are identical or substantially identical among the species. For example, the first primer-binding sites (or reverse complements thereof) of the couplers within a group may have identical or substantially identical sequences. Similarly, the second primer-binding sites (or reverse complements thereof) of the couplers within a group may have identical or substantially identical sequences. Having identical or substantially identical primer-binding sites within a group permits amplification and sequencing of all of the molecular identity tags and associated target nucleic acid sequence on a single sequencing platform. "Substantially identical," used with regard to two substantially identical primer-binding sites, means that sequences have a degree of identity high enough to permit the same primer to bind to both sequences. Sequences that are substantially identical may have at least about 60% identity, at least about 65% identity, at least about 70% identity, at least about 75% identity, at least about 80% identity, at least about 85% identity, at least about 90% identity, at least about 95% identity, or at least about 99% identity. It is known in the art that a considerable amount of mis-matching between a primer and a primer-binding site can occur and still result in primer binding. The degree of permissible mis-matching increases as the primer length increases.

The couplers of the invention preferably have lengths of from about 20 bases to about 10 kilobases. The length of the couplers may be optimized in accordance with the average length of the target nucleic acid insert that is intended to be inserted in order to promote intramolecular ligation. As described above, optimal nucleic acid lengths for promoting intramolecular ligation are well-known.

Although not required, the couplers in a group preferably have the same or substantially the same length. When used in reference to the length of couplers in a group, "substantially the same length" or variants thereof means that each coupler in the group has a length +/−70% of the mean length, +/−60% of the mean length, +/−50% of the mean length, +/−40% of the mean length, +/−30% of the mean length, +/−20% of the mean length, +/−10% of the mean length, +/−5% of the mean length, +/−70% of the median length, +/−60% of the median length, +/−50% of the median length, +/−40% of the median length, +/−30% of the median length, +/−20% of the median length, +1-10% of the median length, or +/−5% of the median length.

Methods of Marking Target Nucleic Acids with Molecular Identity Tags for Distinguishing Intermolecular Products Thereof.

Methods of the invention include marking target nucleic acids with multiple, mutually distinguishable pairs of molecular identity tags as described above. Target nucleic acids suitable for use in the present invention include but are not limited to: genomic DNA of eukaryotic and prokaryotic organisms; microbial DNA; plastid DNA; plasmid and phagemid DNA; viral DNA and RNA; complementary DNA (cDNA) derived from ribonucleic (RNA); and DNA produced by in vitro amplification such as by PCR, among others. Methods for DNA isolation from aforementioned sources, synthesis of cDNA from RNA, and the amplification of nucleic acids are known to those skilled in the art. The target nucleic acids may be fragmented, such as by enzyme digestion, physical shearing, shearing, or other methods.

The target nucleic acids may be marked by ligating nucleic acids comprising molecular identity tags to the target nucleic acid, by amplifying the target nucleic acid using degenerate primers comprising the molecular identity tags on 5' overhangs, or by other methods. Any number of strategies can be used to mark the target nucleic acids, depending on whether the molecular identity tags are physically linked or not prior to the marking.

If the molecular identity tags are not physically linked prior to marking, the target nucleic acids can be divided into multiple aliquots for attaching (e.g., ligating or primer-dependent amplification) a different molecular identity tag or different molecular identity tag pair in each aliquot. Such a strategy can be cumbersome if a large number of molecular identity tag pairs are used. To simplify the marking, large numbers of molecular identity tag pairs can be attached through a combinatorial approach of successive rounds of sample pooling and molecular identity tag attachment. An exemplary version of this approach is shown in FIG. 1, wherein the final molecular identity tags are constructed on the target nucleic acids through segmental attachment. The initial target nucleic acid sample (e.g., DNA) is first divided into a first set of aliquots and a different partial identity sequence is attached to the target nucleic acid in each aliquot. The aliquots are then pooled and subsequently divided into a second set of aliquots, wherein a different partial identity sequence is again attached to the partial identity sequences on the target nucleic acids in each aliquot. The aliquots are then pooled, resulting in target nucleic acids marked with a large number of molecular identity tag pairs. Such a strategy can attach a large number of molecular identity tag pairs with a minimal number of attachment reactions. For example, attaching a different partial molecular identity tag in ten separate aliquots at each of two sequential attachment steps results in 100 functional pairs of distinguishable molecular identity tags using only twenty total attachment reactions. Other combinatorial schemes to generate sequence tags are known in the art (Patterson and Gabriel, *Nature Biotechnology* 27:826-827, 2009).

If the molecular identity tags are physically linked prior to marking, the target nucleic acids can be divided into multiple aliquots for attaching a different molecular identity tag pair in each aliquot. Alternatively, the target nucleic acids can be prepared in a manner described in the examples such that each target nucleic acid will attach to one and only one pair of molecular identity tags. The molecular identity tags can all be pooled and attached by ligation to the target nucleic acids in a single aliquot.

Once the target nucleic acids are marked, intermolecular chimeras resulting from terminal end-joining reactions (such as ligations, sticky-end base-pairing, etc.) with the marked nucleic acids or with products therefrom are capable of being detected and distinguished from the remaining nucleic acids. The end-joining reaction juxtaposes molecular identity tags across the joined terminal ends. The juxtaposed molecular identity tags can be detected by sequencing a region of the end-joined nucleic acid comprising both the juxtaposed molecular identity tags. This is preferably preceded by amplifying the region of the nucleic acid comprising both the juxtaposed molecular identity tags. Nucleic acids comprising paired juxtaposed molecular identity tags are probable intramolecular ligation products. Nucleic acids comprising non-paired juxtaposed molecular identity tags are intermolecular ligation products. The intermolecular ligation products can be excluded from subsequent analysis. In this manner, the intermolecular ligation products (i.e., those containing non-paired juxtaposed molecular identity tags) can be parsed from the remaining nucleic acids (i.e., those containing paired juxtaposed molecular identity tags). "Juxtaposed," used herein to refer to molecular identity tags, refers to two adjacent molecular identity tags, i.e., those that do not have any other molecular identity tags interposed between. The relevant juxtaposed molecular identity tags used to identify intermolecular ligation products are those disposed across the joined terminal ends of the terminal-end joining reaction.

To help locate the joined terminal ends and the juxtaposed molecular identity tags, a nucleic acid comprising a junction code may be used to join the terminal ends. The junction code may comprise any readily recognizable sequence. In some versions, the junction code comprises a palindromic sequence. The junction code may comprise from 2 to about 100 bases, from 2 to about 50 bases, from 2 to about 40 bases, from 2 to about 30 bases, from 5 to about 100 bases, from 5 to about 50 bases, from 5 to about 40 bases, from 5 to about 30 bases, from 10 to about 100 bases, from 10 to about 50 bases, from 10 to about 40 bases, from 10 to about 30 bases, from 15 to about 100 bases, from 15 to about 50 bases, from 15 to about 40 bases, from 15 to about 30 bases, from 20 to about 100 bases, from 20 to about 50 bases, from 20 to about 40 bases, or from 20 to about 30 bases. The junction code preferably does not comprise a sequence identical to any of the molecular identity tags used therewith. An exemplary junction code sequence is 5'-GGT-TCATCGTCAGGCCTGACGATGAACC-3' (SEQ ID NO:5).

The steps described above may be used in making mate-pair libraries and analyzing them. The steps may be incorporated in any method of making mate-pair libraries, including "outside-in" methods (Korbel et al., 2007, *Science* 318:420-426; US 2006/0292611 to Berka et al.), "outside-out" methods (U.S. Pat. Nos. 7,932,029 and 8,329,400 to Lok), cloning-based methods, or non-cloning-based (in vitro) methods. Mate-pairs are also referred in the art as "paired-end tags," "paired-end ditags," or "ditags."

Figure 2:
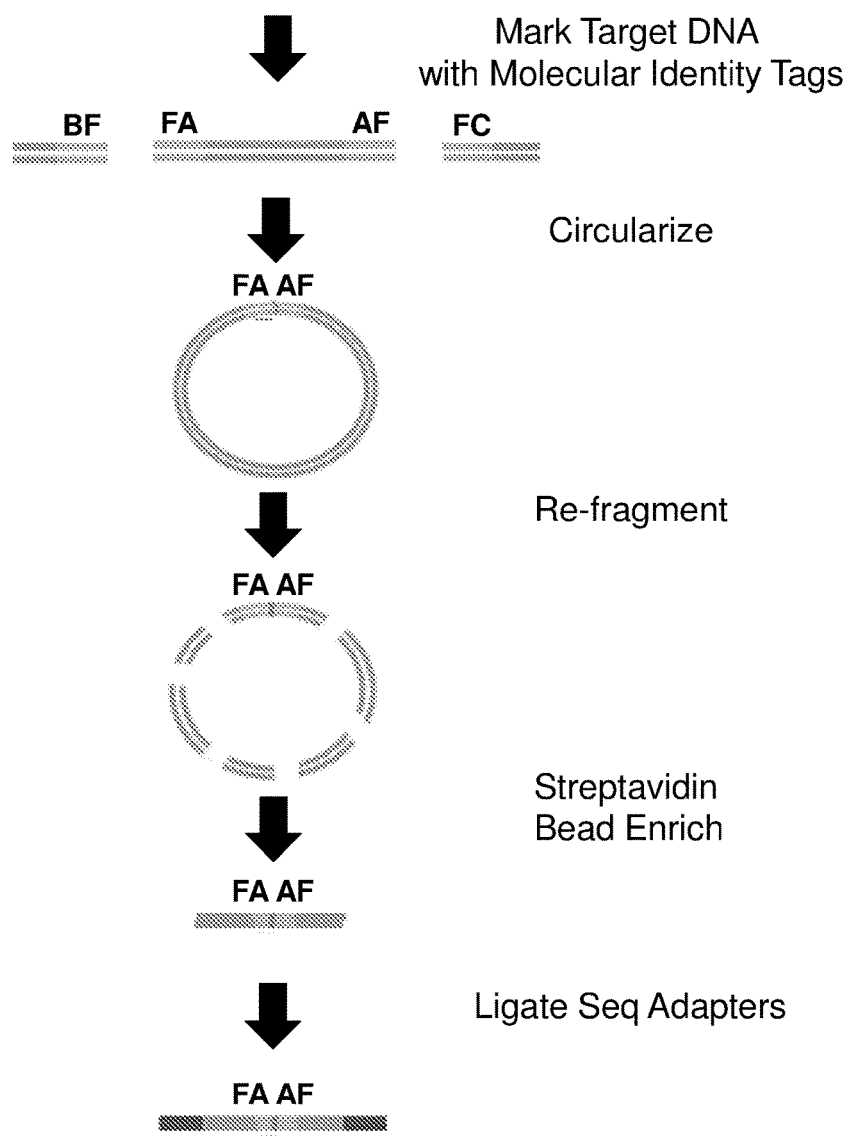
FIG. 2 is a flowchart showing an exemplary "outside-in" method of generating mate pairs marked with molecular identity tags. Molecular identity tags are indicated by letter pairs (BF, FA, AF, and FC).

An exemplary "outside-in" method of making a mate-pair library is shown in FIG. 2. Linear target nucleic acids, which may be fragmented genomic DNA, is marked with molecular identity tags. The molecular identity tags are preferably labeled with a purification label, such as a biotin label, for downstream purification. The marked target nucleic acids are circularized in a ligation reaction, which juxtaposes the molecular identity tags across the joined terminal ends. The circularized nucleic acids are then fragmented into linear fragments, and the fragments comprising the molecular identity tags are recovered, such as by biotin affinity chromatography. At least some of the recovered fragments will have portions of the original target nucleic acids, "insert tags," on the terminal ends. Sequence adapters are then attached (e.g., by ligation) to the terminal ends of the recovered fragments. Sequencing of the fragments can then reveal the identity of the juxtaposed molecular identity tags. The presence of paired molecular identity tags indicates a probable intramolecular circularization in the original ligation reaction and, thus, that the sequenced insert tags are probable true mate pairs. The presence of non-paired molecular identity tags indicates an intermolecular circularization or ligation in the original ligation reaction and, thus, that the sequenced insert tags are not true mate pairs.

Non-physically linked molecular identity tags are preferably used in the "outside-in" method of making a mate-pair library. However, physically linked molecular identity tags may also be used. If physically linked molecular identity tags are used, a linker linking the individual molecular identity tags is preferably excised after marking the target DNA. The linker-excised DNA is then circularized in the ligation reaction to juxtapose the molecular identity tags.

Figure 4:
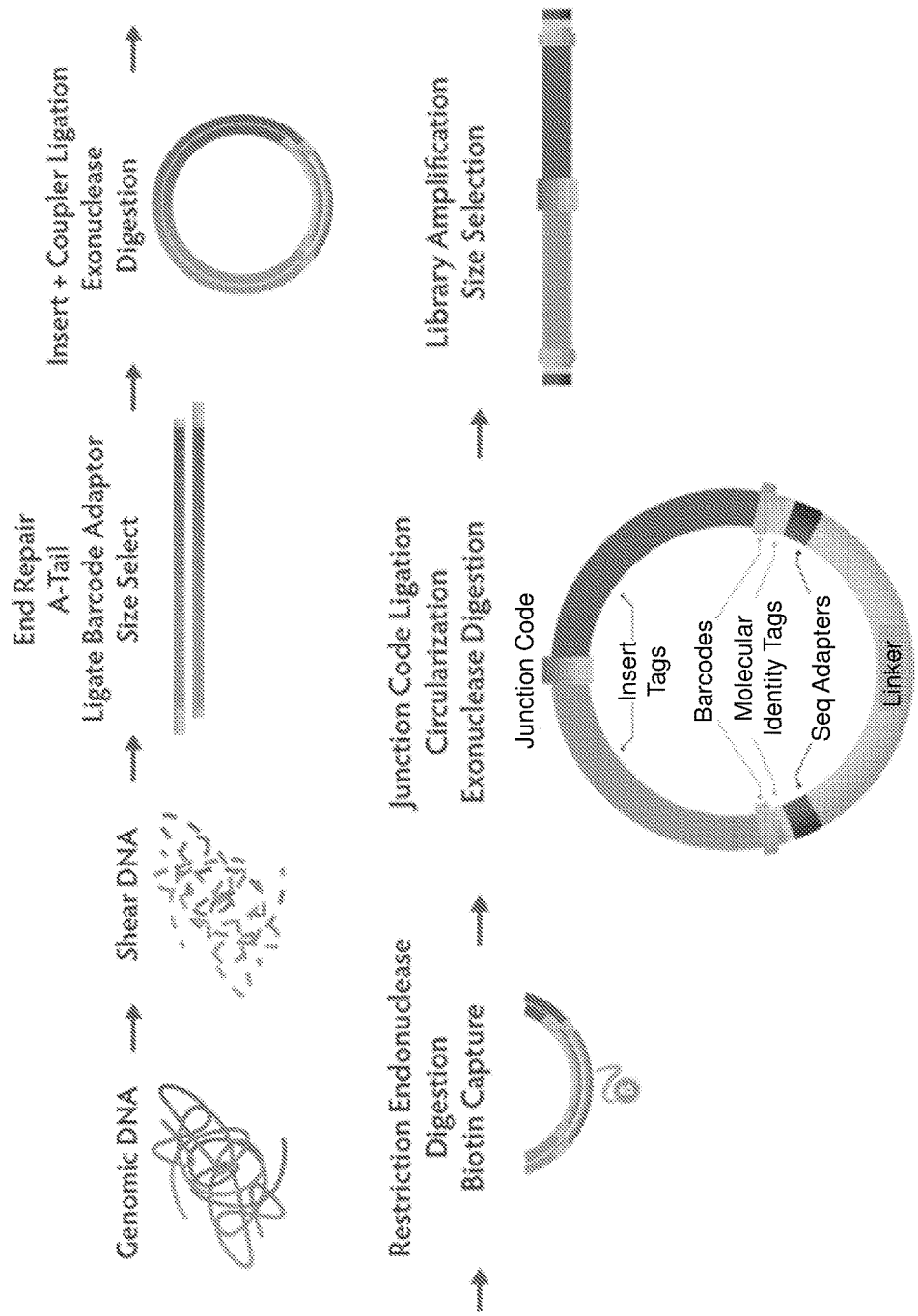
FIG. 4 is a flowchart showing an exemplary "outside-out" method of generating mate pairs marked with molecular identity tags.

An exemplary "outside-out" method of making a mate-pair library is shown in FIG. 4, which is explained in further detail in the following examples. Briefly, linearized target nucleic acids (e.g., sheared genomic DNA) are marked with physically linked pairs of molecular identity tags to generate end-coupled, marked nucleic acid species. The target nucleic acid insert in the end-coupled, marked nucleic acid species are excised through digestion, leaving insert tags attached to the molecular identity tags. The molecular identity tags with insert tags are then recovered, preferably through biotin affinity chromatography. The recovered species are then circularized in a ligation reaction to juxtapose the molecular identity tags and the sequences tags across the joined terminal ends. The circularized species can then be amplified into linear species, and the linear species can be sequenced. The presence of paired molecular identity tags indicates a probable intramolecular circularization in the original ligation reaction and, thus, that the sequenced insert tags are probable true mate pairs. The presence of non-paired molecular identity tags indicates an intermolecular circularization or ligation in the original ligation reaction and, thus, that the sequenced insert tags are not true mate pairs.

A more detailed description of methods of generating and analyzing mate-pair libraries with the molecular identity tags of the invention are described below.

Preparation and Fragmentation of Nucleic Acids for Production of Mate Pairs.

Target nucleic acids suitable for use in producing mate pairs include but are not limited to: genomic DNA of eukaryotic and prokaryotic organisms; microbial DNA; plastid DNA; plasmid and phagemid DNA; viral DNA and RNA; complementary DNA (cDNA) derived from ribonucleic (RNA); and DNA produced by in vitro amplification such as by PCR, among others. Methods for DNA isolation from aforementioned sources, synthesis of cDNA from RNA, and the amplification of nucleic acids are known to those skilled in the art.

For certain embodiments, the physical distance spanned by the mate pair along the length of the target DNA determines the resolution level for analysis. The smaller the spacing between mate pairs, the higher is the spatial resolution for mapping and for detecting fine-structural-variations within a target population of nucleic acids. Larger mate-pair spacing requires fewer mate pairs to provide physical coverage a DNA sample of a given complexity but with a concomitant decrease in spatial resolution to detect small genomic structural variants. Large mate-pair spacing spans large repetitive regions to facilitate de novo genomic assembly and the analysis of large structural alternations in DNA. The ability to produce mate-pairs of 5-, 10-, 25-, 50-, 100-kb, or more separation distance allows the end-users to choose functional tradeoffs between mate-pair spacing, resolution level required to detect different types of DNA structural variations, and the number of mate pairs needed to provide adequate physical coverage for a genome of a given complexity. The optimal number and the proportion of mate pairs of different spacing can be modeled computationally for specific applications.

The physical length of target DNA insert used for the construction of mate pairs governs the separation distance between each of a given pair. Methods to create and to purify a near-homogeneous size population of fragmented nucleic acid molecules are described in the art. Fragmenting a target DNA population to a desired insert length can be accomplished enzymatically under conditions of partial or complete digestion with a variety of restriction endonucleases. The use of restriction endonuclease with recognition sites of six or greater base pairs are useful to produce longer DNA fragments. The use of one or more restriction endonucleases with different sensitivity to DNA methylation can be used to assess the DNA methylation status of the target DNA population. The use of frequent cutting type II restriction endonucleases such as Mbo I, Hae III, and the like, which cut DNA once on average every 256-bp (based on random distribution and equal representation of the four bases in the target DNA), is known in the art for producing varied sizes of DNA fragments by partial digestion. The use of restriction endonuclease CviJ I under relaxed conditions, which cleaves DNA at GC dinucleotide positions (Fitzgerald et al., 1992), is particularly useful under partial digestion conditions to produce a useful continuum of DNA fragment sizes. In some embodiments, randomly generated DNA fragments are useful. Methods for generation of random DNA fragments include: (1) Digestion with bovine pancreatic deoxyribonucleic acid nuclease I (DNase I), which makes random double-strand cleavages in DNA in the presence of manganese ions (Melgar and Goldthwait, 1968; Heffron et al, 1978); (2) Physical shearing (Shriefer et al, 1990); and (3) Sonication (Deininger, 1983).

Conditions for partial enzymatic digestion are determined empirically, varying one or more parameters of reaction volume, enzyme concentration, and enzyme to substrate ratio, incubation time, or temperatures. Mate-pair separation of 5-kb or less, fragmentation methods that are not sequence dependent are preferred. Bovine pancreatic DNase I makes random double-strand cleavages in DNA in the presence of manganese ions (Melgar and Goldthwait, 1968; Heffron et al, 1978) and can be used for this purpose. Likewise, DNA fragmentation by mechanical means such as sonication, or the selective application of shear forces can also be used. The HYDROSHEAR instrument (Genomic Solutions Inc., Ann Arbor, Mich.) or the COVARIS (Covaris Inc., Woburn, Mass.) instrument employing Adaptive Focused Acoustics are particularly useful for generating random DNA fragments of a defined size range. Random DNA fragments can also be generated through the use of random primers during cDNA synthesis or during PCR, alone or in combination with the other fragmentation methods described.

The progress of fragmentation to yield the desired length product is easily monitored by gel electrophoresis. Following generation of a suitable DNA size-distribution, T4 DNA polymerase is used to repair or to make blunt the target DNA ends in preparation for blunt-end ligation to a coupler (vector or nucleic acid backbone) or insertion adapters for the production of the mate pairs. In cases where DNA is fragmented by partial or complete digestion with one or more endonucleases leaving cohesive ends, repair is not necessary, but the design of the insertion adapter, and/or coupler will need to accommodate the particular cohesive ends generated by the fragmentation enzyme. Since ligation of target DNA inserts to other target DNA inserts destroys the co-linearity of the sample and undermines the construction of genomic maps, the 5' phosphate groups of the target DNA are removed by a phosphatase to prevent the creation of chimeric DNA inserts during ligation to the insertion adapter or to the coupler.

Size Fractionation and Purification of Size-Selected DNA.

For certain embodiments, dephosphorylated DNA inserts are fractionated by gel electrophoresis or by high performance liquid chromatography (HPLC) to yield purified DNA inserts of a desired size. Polyacrylamide gels are best used for fractionation of DNA from 50-bp to 1-kb. For fragment sizes of ~250 bp to ~50 kb, 0.4% to 3% agarose gels are suitable. Pulsed field gel electrophoresis is suitable for fractionating DNA from ~10-kb to several hundreds of kb in size. These procedures have been described (Rickwood and Hames (eds.), In: Gel Electrophoresis of Nucleic Acids—A Practical Approach, Oxford University Press, New York, 1990; Hamelin and Yelle, 1990; Birren and Lai, In: Pulse Field Electrophoresis: A Practical Guide, Academic Press, San Diego, 1993). DNA is sized with the use of suitable size markers electrophoresed in parallel with the sample and are visualized by staining. Gel slices containing DNA of a desired size are excised with a scalpel, after which the DNA is recovered from the gel matrix by electro-elution or by enzymatic or chemical degradation of the gel matrix. The recovered DNA fragments for analysis should be near homogeneous in size. Gel systems and electrophoretic conditions for maximizing separation resolution are known in the art. Two or more cycles of gel electrophoresis may be used to obtain greater sample size homogeneity. Samples with size variance of more than 2.5% to 5% from the mean length may contribute to noise.

Design of Insertion Adapter and Ligation of Target DNA to Coupler.

In some embodiments, each marked or unmarked target DNA insert is first ligated to insertion adapters to facilitate its ligation to a coupler (e.g., a vector or a nucleic acid backbone). In other embodiments, each marked or unmarked target DNA insert is ligated directly to a coupler without using insertion adapter intermediates. If unmarked target DNA inserts are ligated to couplers, the couplers themselves preferably comprise molecular identity codes as described above. In yet other embodiments, individual insertion adapters are first ligated to each ends of marked target DNA whereupon the free ends of the newly ligated insertion adapters are re-circularized to form a functional nucleic acid backbone for the subsequent generation of a mate pair.

Insertion adapters may incorporate moieties such as biotin groups to facilitate affinity purification of the desired DNA products. Insertion adapters may also incorporate restriction endonuclease recognition sites for the excision of the generated mate pair from the nucleic acid backbone or the incorporation of nuclease recognition sites for type IIS, IIG or type III endonucleases to create the mate pair by cleavage of the ligated target DNA insert. For mate-pair generation where the target DNA insert is ligated directly to the vector or to the nucleic acid backbone, the appropriate recognition sites for the aforementioned type IIS, IIG or type III restriction endonucleases may be incorporated into the design of the vector or the nucleic acid backbone. Another aspect of the present invention makes use of one or more type II restriction endonucleases to digest the ligated target DNA insert to create mate pairs that are attached to each ends of a vector or nucleic acid backbone, where the said vector or the nucleic acid backbone are designed to be free of those digestion sites and remains undigested.

Those skilled in the art would realize the existence of a plurality of insertion adapter designs suitable for execution of the present invention. In general, a suitable insertion adapter comprises the following material properties: (1) a short top strand and a short bottom strand of 5' phosphorylated oligonucleotides capable of stable complementary base-pairing to yield a two-strand structure; (2) one end of the insertion adapter has a cohesive extension (non-palindromic is preferred) that ligates to a vector, to a nucleic acid backbone, or to another insertion adapter having the complementary sequence; (3) the other insertion adapter end has a blunt-end structure or other suitable end structures to enable efficient ligation to the target DNA fragments (dephosphorylated target DNA is preferred); (4) for some embodiments, the end of the insertion adapter flanking the target DNA insert may bear a suitable type IIS, type IIG or type III restriction endonuclease recognition site in an orientation such that the site directs cleavage within the target DNA at a fixed and useful distance from the target DNA terminus to produce a mate pair (for reviews of the type IIS, IIG and III restriction endonucleases, see Sistla and Rao (2004), Bujnicki (2001), Szybalski et al (1991); (5) for some embodiments, the insertion adapter may bear a second restriction endonuclease site for excising the created mate pair from the vector; and (6) for some embodiments, the insertion adapter may bear a barcode.

A barcode is a short nucleic acid sequence used as an identifier to mark individual samples to enable pooling of multiple samples to achieve cost saving or improved workflow efficiency. See Craig et al., Nature Methods 5:887-893, 2008; Kivioja et al., Nature Methods 9:72-76, 2012; Fodor et al., US 2011/0160078A1; and Fullwood et al., Nature 462:58-64, 2009, for various uses of barcodes. Barcodes are useful for "multiplexing" the generation, sequencing, and analysis of mate pairs derived from more than one unique target nucleic acid. For example, fragmented DNA from each of multiple individual originating DNA samples may be ligated with insertion adapters comprising one or more unique barcodes. The fragmented, barcoded DNA can then be pooled and undergo subsequent mate-pair generation, sequencing, and analysis steps. The unique barcodes can then be detected at the analysis stage to link the resulting mate pairs with the originating DNA samples. See, e.g., Craig et al. Nature Methods 5:887-893, 2008. Exemplary barcode sequences for use in the present invention include CTAAGGTAA, TAAGGAGAA, TTCCGATAA, TGAGCGGAA, CTGACCGAA, TCTAACGGA, TCTGGATGA, TTAGTCGGA, TGCCACGAA, CCTGAGATA, TCTTACACA, and TCAGGAATA. Any other unique sequences can be used in the present invention as a barcode.

Those of skill in the art know methods for ligating nucleic acid molecules, such as ligating insertion adapters to DNA inserts. See, for example, Ausubel et al. (eds.) (In: Short Protocols in Molecular Biology, 3rd Ed, John Wiley & Sons, New York, 1995). Typical ligation conditions for efficient blunt-end ligation of insert adapter to DNA insert call for a ~50- to several hundred-fold molar excess insertion adapter to target DNA, high T4 DNA ligase concentration, or the inclusion of a volume exclusion agent such as polyethylene glycol (Hayashi et al, 1986; Pheiffer and Zimmerman, 1983; Zimmerman and Pheiffer, 1983). Efficient ligation of insertion adapter to cohesive end target DNA requires ~five-fold molar excess. Insertion adapter-ligated DNA inserts are preferably passed through a CHROMOSPIN column (Clontech, Mountain View, Calif.) or otherwise cleaned to remove excess insertion adapters before purification and size-selection by gel electrophoresis. To generate mate pairs by intramolecular ligation, the purified insertion adapter-ligated target DNA inserts are ligated into one of several plasmid vectors and nucleic acid backbones as described below.

According to an aspect of the present invention, any restriction endonucleases, preferably a frequent cutting type II restriction endonuclease, that preferentially cleave the target DNA insert and not the vector, the nucleic acid backbone or any insertion adapters to which the target DNA is ligated, are suitable for use in the generation of mate pairs. REBASE, the restriction enzyme database, provides information of the type II restriction endonucleases, isoschizomers, neoschizomers, recognition sequences, commercial availability and references (rebase.neb.com). Preferred type II restriction endonucleases are those that cut the target DNA insert frequently, such as enzymes that recognize 4-base pair sites, thereby creating insert tags of average lengths of 100- to 300-bp. Type II restriction endonucleases FspB I or Csp6 I, alone or in combination, are particularly suited for use by the present invention to generate mate pairs since these two enzymes cut frequently and produce the identical complementary cohesive ends allowing the direct production of a mate pair of the present invention by intramolecular ligation without modifications to the ends. Other restriction endonucleases that only cleave the target DNA insert but not the coupler or the insertion adapters to which the target DNA insert is attached, are considered within the scope and spirit of the present invention.

Vectors and Nucleic Acid Backbones for Mate-Pair Production.

In some embodiments where large mate pair-spacing is required, it may be desirable to propagate the target DNA in a host cell prior to the creation of the mate pair. Rearrangement or loss of target DNA segments containing AT- or GC-rich sequences, repeats, hairpins, strong promoters, toxic genes and other problem sequences when propagated in host cells are of concern. DNA rearrangements and other cloning artifacts can be mistaken for structural variations in the target nucleic acid. Moreover, cloning bias can limit the size of inserts and can under-represent important regions of the genome under study. This problem was addressed recently with the development of fosmid and BAC vectors with conditional amplification (Szybalski, U.S. Pat. No. 5,874,259) where propagation of DNA is kept at one to two copies per host cell until induced to higher levels for analysis. Improved stability of genomic inserts of 15-kb to over 100-kb was reported and conditional amplification vectors are now in routine use for genomics studies. Conditional amplification fosmid/BAC vectors such as pCCI-FOS (Epicentre, Madison, Wis.), pSMART-VC (Lucigen, Middleton, Wis.), PNGS FOS (Lucigen) and their variants are suitable for use in mate-pair production of spacing from 10-kb to 200-kb. However, use of conventional low-copy plasmid vectors appear to be sufficient for stable maintenance of large DNA fragments without the need of BAC, PAC or fosmid type vectors (Feng et al, 2002; Tao and Zhang, 1998). The pSMART series of vectors offers low copy number propagation and has the added feature of having transcription terminators on the vector to reduce the potential effects of transcriptional interference, which might further improve DNA stability (Mead and Godiska, U.S. Pat. No. 6,709,861). For mate-pair production with spacing on original insert of 10-kb or more, a variety of established and widely used low copy plasmid-based vectors are suitable to produce mate pairs, including: pBR322 (Bolivar et al, 1977), pACYC177 (Chang and Cohen, 1978) and others described in the present disclosure. Molecular identity tags can be incorporated in any of the vectors described above or known in the art. Alternatively, any of the elements contained in the vectors described above or known in the art can be incorporated in the couplers of the present invention.

Nucleic acid backbones used to create mate pairs by intramolecular ligation can be created by direct chemical synthesis to any desired specification. Subsequent large-scale production of a nucleic acid backbone can be produced by chemical synthesis or in part or in whole by PCR from a template. The nucleic acid backbone may contain only a minimal sequence comprising molecular identity tags, sequence adapters, and/or insertion adapters as described herein. Biotin and other affinity tags moieties can also be incorporated into the nucleic acid backbone, such as in the linker, to enable affinity purification of DNA intermediates in the different steps of in vitro mate-pair production. One particularly useful design comprises a synthetic nucleic acid backbone that is free of all or most of the sixteen possible four-base-pair palindromes. Such a nucleic acid backbone allows the generation of mate pairs by digestion of the ligated target DNA insert with nearly any four-base recognition restriction endonuclease, alone or in combination, without cleavage to the nucleic acid backbone or adapter. Another particularly useful nucleic acid backbone design incorporates sequences that are compatible with DNA amplification and sequencing primer binding for use in the next generation DNA sequencing platforms for massively parallel high throughput DNA sequencing of the generated mate pairs. The nucleic acid backbone is preferably long enough either to provide primer binding sites for the amplification of the created mate pair, to effect affinity purification, to enable efficient attachment (ligation) to the target DNA, or to at best be a unique identifier in providing a reference point.

For generating mate pairs, the vector or nucleic acid backbone to which the target DNA is ligated should be free of cleavage sites for the restriction endonuclease used to generate the mate pairs from the target DNA insert. Cleavage of the vector or the nucleic acid backbone would destroy the spatial linkage of the mate pairs and would prevent the creation of the mate pair by intramolecular ligation. A vector or nucleic acid backbone can be made free of unwanted restriction sites by site-directed mutagenesis employing standard methods. See, for example: McPherson (ed.) (In: Directed Mutagenesis—A Practical Approach, Oxford University Press, New York, 1991) and Lok (U.S. Pat. No. 6,730,500). Typically, a substantial portion of a vector or nucleic acid backbone can be altered by single base-pair change to eliminate unwanted restriction endonuclease recognition sites without due effects on functionality. Within protein coding sequences, single nucleotide changes are targeted to the codon wobble positions to maintain native protein coding Changes made elsewhere on the vector or the nucleic acid backbone would require functional validation before use. Many restriction endonucleases are sensitive to methylation of their recognition sites, in particular, methylation at the 5-carbon position of deoxycytosine can render those sites on the vector or the nucleic acid backbone free from digestion. DNA methylation can be accomplished through direct incorporation of 5-methy-dCTP by PCR, passage of DNA through appropriate host cells with different restriction modification systems, or by use of specific methylases to render restriction sites on the vector or nucleic acid backbone retractile to enzymatic cleavage. REBASE, the restriction enzyme database, provides information of the methylation sensitivity of restriction endonucleases, (rebase.neb.com).

Mate-Pair Production.

In certain embodiments, a population of target DNA for mate-pair production is fragmented randomly by mechanical or enzymatic means to produce fragments of a desired size for mate-pair production. In other embodiments, a target DNA population is digested to completion with one or more restriction endonucleases in separate reactions or in combination to cleave target DNA at specified sites. In yet another embodiment, target DNAs are digested to completion with one or more restriction endonucleases and are then fractionated to a desired size. For target DNA digested with enzymes that create cohesive ends, the dephosphorylated target DNA may be cloned directly into a suitably modified vector or nucleic acid backbone. Fragmented target DNA having "ragged" ends are repaired using T4 DNA polymerase or mung bean nuclease and are then dephosphorylated to prevent the creation of chimeric target DNA inserts. Likewise, target DNA bearing cohesive ends is also dephosphorylated to prevent the creation of chimeric inserts. Where ligation of target DNA to vector or nucleic acid backbone is carried out with the use of insertion adapters, CHROMASPIN columns (Clontech, Mountain View, Calif.) are preferably used to remove unligated insertion adapter before ligation of adapter-ligated target DNA to a mate-pair production vector. In certain embodiments, target DNA are size-selected to a desired length by gel electrophoresis or by other means prior to mate-pair production.

As used herein, cosmid, fosmid, phagmid, BAC and other episomal elements are referred collectively as vectors. Ligation conditions for optimizing intermolecular ligation of a vector or a nucleic acid backbone to an insert followed by intramolecular ligation to yield a circular molecule have been described for DNA segments over a range of fragment lengths (Collins and Weissman, 1984; Dugaiczyk et al, 1975; Wang and Davidson, 1966). General methods for ligating nucleic acid molecules, transfection into host cell and for construction of plasmid-based libraries are known to those who are skilled in the art. See, for example, Sambrook et al (In: Molecular Cloning: A Laboratory Manual 2nd Ed, CSH Press, New York, 1989); Ausubel et al, (eds) (In: Short Protocols in Molecular Biology, 3rd Ed, John Wiley & Sons, New York, 1995); Birren et al (In: Bacterial Artificial Chromosomes in Genome Analysis—A Laboratory Manual, CSH Press, New York, 1999). Ligated target DNA is introduced into host cells by electroporation or by transfection. Alternatively, target DNA inserts of 45- to 50-kb ligated onto a suitable cosmid vector are transduced into host cells after in vitro phage packaging using an appropriate commercially available packaging extract (Stratagene, La Jolla, Calif.). Propagation of methylated target DNA such as genomic DNA or cDNA synthesized by certain protocols that make use of methylated nucleotide analogues requires host cell strains with inactive mcr and mrr alleles. Suitable host strains include: 10G (Lucigen, Middleton, Wis.); XL1-Blue MR and XL2Blue MRF' (Stratagene, La Jolla, Calif.). Electroporated, transfected or transduced cells are plated onto 10-cm diameter agar plates at a density of ~20,000 to 50,000 colonies per plate under the appropriate drug selection to yield the primary library. An alternative method is to grow the transduced or transfected cells in liquid culture while exercising care not to overgrow cells to encourage undesirable clonal selection. The total number of clones under culture should reflect the number of mate pairs required by the study design. Cells are harvested and the plasmids isolated for the subsequent step described below.

In an aspect of the invention, vectors or nucleic acid backbones bearing target DNA insert are digested to completion with FspB I or Csp6 I (Fermentas Inc., Hanover, Md.) to generate mate pairs. The resulting digestion cleaves the insert DNA to generate the mate pairs without cleavage to the attached vector or nucleic acid backbone. Mate pairs generated in this manner are variable in size, dependent on the average frequency of cut sites within the target DNA and the distance of the first cut site from the target DNA termini. Mate pairs produced by FspB I or Csp6 I digestion of randomly fragmented human DNA inserts are expected to have an average length of 100- to 200-bp. Linearized vector or nucleic acid backbone with the newly created mate pairs attached are purified away from the milieu of digested insert DNA fragments, by gel electrophoresis or by affinity chromatography. Purified linear products are circularized to yield the primary mate-pair library. Mate pairs can be recovered from the circularized templates by DNA amplification for direct DNA sequencing. Alternatively, circularized vector bearing mate pairs are introduced into host cells and plated at a density of ~20,000 to 50,000 colonies per 10 cm plate or are grown in liquid culture under selection to yield a primary plasmid mate-pair library. Purified plasmids from the plasmid primary mate-pair library are digested with enzyme that cleaves both sides of the mate pairs to excise the mate pair from the vector for direct DNA sequencing. Alternatively, the mate pairs are amplified from primer-binding sites on the plasmid.

In Vitro Mate-Pair Production.

Mate pairs may be generated in vitro without propagation steps through a host cell. Generally, nucleic acid backbones suitable for generation of mate pairs without propagation through a host cell should be at least 50- to 100-bp or more in length in order to have sufficient segmental flexibility to undergo intramolecular ligation to yield a circular molecule for creating the mate pair. Nucleic acid backbones for in vitro mate-pair production need not necessarily contain a replication origin or a drug selection marker. Such nucleic acid backbones should possess suitable PCR primer binding sites flanking the mate pair and the molecular identity tags for amplification of the created mate-pair and associated molecular identity tags. The nucleic acid backbone may be derived in part or in whole from restriction endonuclease digestion of an engineered plasmid. Suitable nucleic acid backbones can also be produced, in part or in whole by PCR, or by direct chemical oligonucleotide synthesis. In cases where the nucleic acid backbone is derived from PCR or from chemical synthesis, modified nucleotides can be incorporated into the nucleic acid backbone for additional functionality. For example, a biotin moiety can be incorporated into the nucleic acid backbone to enable affinity purification of DNA intermediates in the different steps of in vitro mate-pair production. One particularly useful DNA design comprises a nucleic acid backbone that is essentially free or depleted of the sixteen possible four-base-pair long palindromes, allowing the generation of mate pairs by digestion of attached target DNA insert with nearly any four-base recognition restriction endonucleases. Nucleic acid backbones may also include primer-binding sites and other sequences for clonal amplification of DNA templates for DNA sequencing on the next-generation DNA sequencers.

Advantages of Molecular identity tags in Generating Mate Pairs

The use of molecular identity tags in generating mate pairs is advantageous where the presence of artifacts needs to be minimized. A major source of artifacts stems from the intramolecular ligation step to generate the mate pair, where target inserts of two different vectors or nucleic acid backbones are joined by intermolecular ligation. Specifically, target inserts from two different target DNAs are joined to create an artifact mate pair following PCR amplification. General ligation conditions for optimizing intermolecular and intramolecular ligation have been described for DNA segments over a range of fragment lengths (Collins and Weissman, 1984; Dugaiczyk et al, 1975; Wang and Davidson, 1966) to derive optimal conditions to produce circular molecules for in vitro mate pair production. Nevertheless, the chance occurrence of unwanted ligation events could not be entirely eliminated in practice. However, the majority of artifact mate pairs can be purged in silico by virtue of using the molecular identity tags of the present invention, making this approach the method of choice for applications such as de novo genomic assembly where sequence co-linearity of mate pairs is paramount.

EXAMPLES

Preparation of 2 kb, 5 kb, and 8 kb E. coli DH10B Mate-Pair Libraries

Mate-pair libraries were prepared in a manner shown in FIG. 4.

Figure 3:
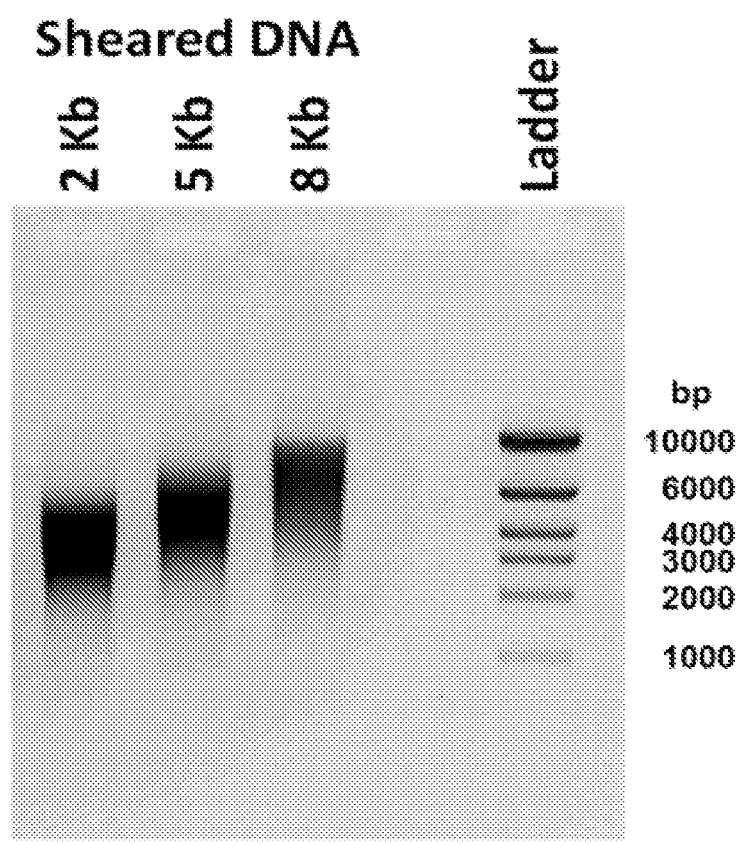
FIG. 3 depicts a DNA gel of genomic DNA from *E. coli* strain DH10B randomly sheared to approximately 2 to 4 kb (2 kb library), 4 to 7 kb (5 kb library), and 8 to 12 kb (8 kb library).

Purified genomic DNA from E. coli strain DH10B was randomly sheared to approximately 2 to 4 kb (2 kb library), 4 to 7 kb (5 kb library), and 8 to 12 kb (8 kb library) with a MEGARUPTOR instrument (Diagenode Inc., Denville, N.J.) following manufacturer's protocol (see FIG. 3). The sheared DNA was cleaned with an equal volume of AGENCOURT AMPURE XP magnetic beads (Beckman Coulter, Inc., Indianapolis Ind.) and eluted in 10 mM Tris pH 8.5 (Elution Buffer). Cleaned DNA was then end repaired in End-Repair Tailing Buffer with an enzyme mixture (Lucigen Corp., Middleton, Wis.) at 25° C. for 20 min. The enzymes were then heat inactivated at 72° C. for 25 min. The end-repaired DNA was A-tailed by adding Klenow DNA polymerase to the above reaction and incubating at 37° C. for 20 min, followed by an enzyme inactivation step at 70° C. for 15 min. The tailed DNA was next ligated at both ends with a barcoded (TAAGGAGAA) insertion adapter that contains both a 3' T-tail and, at the opposite end, a 3' ACAC overhang. The ligated DNA was size selected with AGENCOURT AMPURE XP magnetic beads to remove small DNA fragments below 2 kb (2 kb library) and 4 kb (5 kb and 8 kb libraries).

The fragmented and adapted insert DNA was ligated with T4 DNA Ligase to 2-kb couplers for 16 hrs at 16° C. to form circular molecules containing insert and coupler. A pool of 12 different couplers was used in the ligation reaction. See FIGS. 8A-8L. Each coupler included 3' TGTG overhangs complementary to the insert overhangs (ACAC), sequencing platform-specific adapter sequences for either the ION TORRENT ION PGM (Life Technologies, Carlsbad, Calif.) (SEQ ID NOS:1 and 2) or the ILLUMINA MISEQ and HISEQ (Illumina, Inc., San Diego, Calif.) (SEQ ID NOS: 3 and 4) next-generation sequencing instruments, a biotinylated linker (SEQ ID NO:6), and molecular identity codes for detection of false junction formation during ligations. These elements were configured on the coupler in the manner shown in FIG. 5. The molecular identity codes were comprised of paired 6-mers that were integrated into the couplers. See Table 1 and FIGS. 8A-8L. Each coupler included two unique chimera codes capable of identifying that coupler and distinguishing it from the other 11 couplers. After ligation of insert and coupler, the reaction was digested with exonucleases at 37° C. for 30 min to remove any linear DNA and preserve any circular molecules. The reaction was heat inactivated at 80° C. for 30 min and cleaned with AGENCOURT AMPURE XP magnetic beads.

TABLE 1

Molecular identity tag (MIT) pairs and sequences thereof

| MIT Pair | MIT Sequences | |
|---|---|---|
| A, B | A<br>TGGACT | B<br>TCTGGA |
| C, D | C<br>ACTTCG | D<br>TGATGT |
| E, F | E<br>TGAGTC | F<br>TCGTGA |
| G, H | G<br>TGACTG | H<br>GTGCTA |
| I, J | I<br>TCAGGT | J<br>GAGGTT |
| K, L | K<br>ATGTCA | L<br>AGTTGT |
| M, N | M<br>GTATGA | N<br>TTAGAC |
| O, P | O<br>GTCTAC | P<br>CGTGTA |
| Q, R | Q<br>GTTGGA | R<br>GTTCTC |
| S, T | S<br>CGATTC | T<br>AATCTC |
| U, V | U<br>GGTTAC | V<br>TAGGTC |
| W, X | W<br>TCACCT | X<br>GAGTCT |

The circularized insert/coupler was next digested with one or more restriction enzymes (AluI, RsaI, HpyCH4V, HaeIII, AccII or CviJI) at 37° C. for 30 min, followed by incubation at 80° C. for 15 min to remove the central part of the insert and leave terminal insert tags connected to the coupler. Biotin capture with streptavidin magnetic beads (DYNABEADS MYONE Streptavidin C1, Life Technologies) was then used to purify the coupler and ligated insert tags away from contaminating insert fragments. The 3' ends of both insert tags were G-tailed with Tailing Buffer and Klenow polymerase at 37° C. for 30 min and a C-Tailed junction code adapter (GGTTCATCGTCAGG, bases 1-14 of SEQ ID NO:5) was then ligated to each tag. The junction code adapter-ligated DNA was purified with AGENCOURT AMPURE XP magnetic beads.

Figure 6:
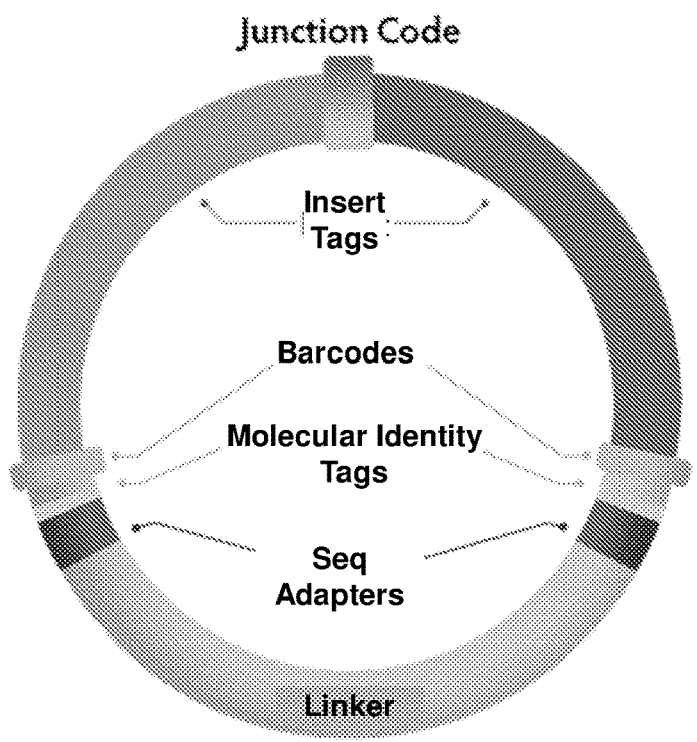
FIG. 6 is a schema depicting a circularized coupler of FIG. 5 with target nucleic acid insert tags and a junction code ligated between the molecular identity tags.

The purified sample junction code adapter-ligated DNA was treated with T4 Polynucleotide Kinase, and the molecules were circularized with T4 DNA Ligase at 25° C. for 30 min to yield structures as shown in FIG. 6

Figure 7A:
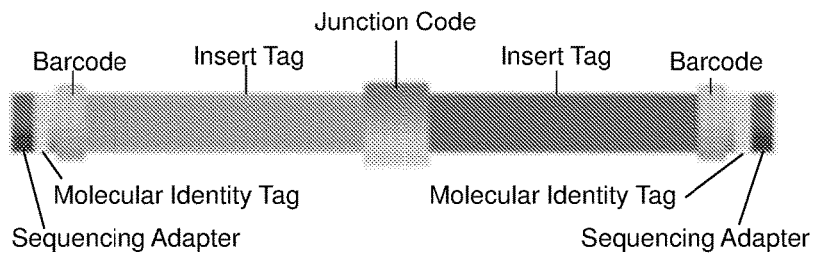
FIG. 7A is a schema depicting an amplicon of the circularized coupler of FIG. 5, generated by amplification using the sequencing adapters.
Figure 7B:
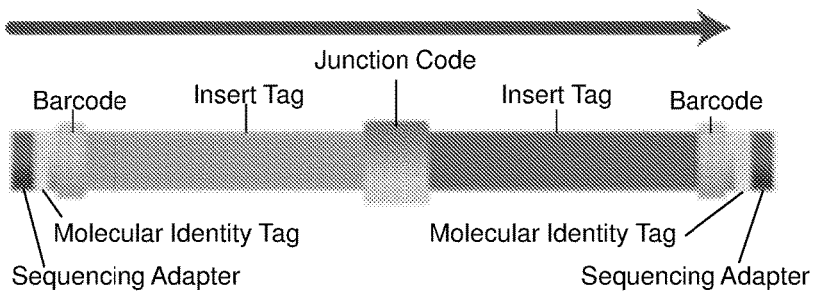
FIG. 7B is a schema depicting a sequencing read of the amplicon of FIG. 7A using an exemplary sequencing platform.
Figure 7C:
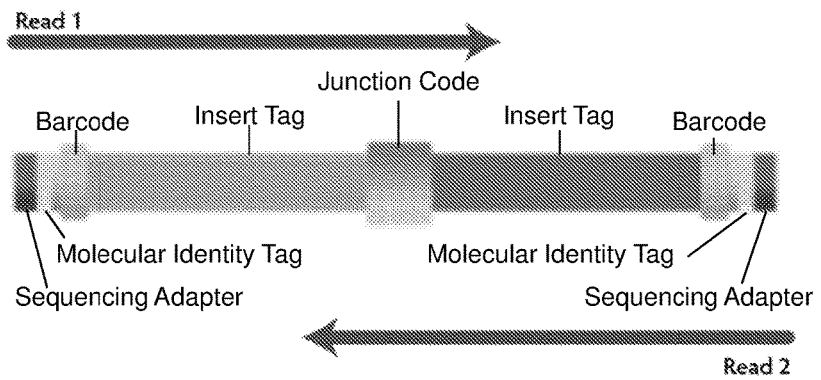
FIG. 7C is a schema depicting sequencing reads of the amplicon of FIG. 7A using an exemplary sequencing platform.
Figure 8A:
FIGS. 8A-8L are schemas depicting different species of couplers with each coupler (solid line) comprising a different pair of molecular identity codes (letters A-X).
Figure 8B:
Figure 8C:
Figure 8D:
Figure 8E:
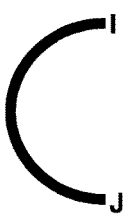
Figure 8F:
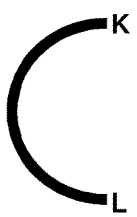
Figure 8G:
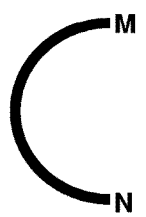
Figure 8H:
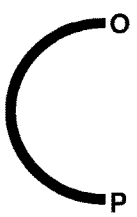
Figure 8I:
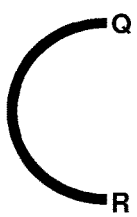
Figure 8J:
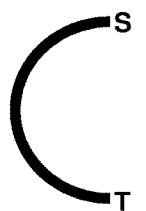
Figure 8K:
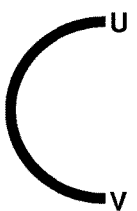
Figure 8L:
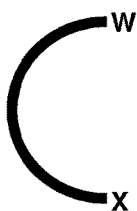

The sample was then purified with AGENCOURT AMPURE XP magnetic beads and amplified with ACCURA Hot Start Master Mix (Lucigen Corp.) and adapter sequence primers to yield structures as shown in FIG. 7A. The amplified DNA was then size selected to 465 bp for ION TORRENT sequencing with a Pippin Prep instrument (Sage Science Inc., Beverly, Mass.), or to 300-700 bp with AGENCOURT AMPURE XP magnetic beads for ILLUMINA sequencing. Platform-specific manuals were used for sequencing reactions using the ION TORRENT (FIG. 7B) or ILLUMINA (FIG. 7C) platforms.

Analysis of Sequence Data.

A set of Python scripts was written to filter and parse the raw reads from ION TORRENT or ILLUMINA sequencing instruments, yielding clean output reads that can be used as input to all of the current open-source and commercial sequence assembly programs. These scripts were run sequentially to perform the following tasks: (1) Analyze reads for presence of barcodes and sort according to barcode, accomplishing de-multiplexing; (2) Analyze reads for presence of molecular identity codes and to classify mate pairs as "mates" (contain molecular identity codes on both ends of the ION TORRENT read, or in Read 1 and Read 2 of the ILLUMINA reads), "true mates" (matching molecular identity codes on both ends of the ION TORRENT read or in both R1 and R2 of the ILLUMINA reads), "chimera" (non-matching molecular identity codes on both ends of the ION TORRENT read or in both R1 and R2 of the ILLUMINA reads), or "other"; and (3) Split the true-mate reads into right and left di-tag reads by detecting the junction code and trimming away the molecular identity codes, barcode, and junction code.

The structure of the raw sequence output (and the types of sequencing errors within the raw output) differ according to instrument platform. Ion Torrent reads are single ended (FIG. 7B) and always begin with the molecular identity code, left barcode (if present), and left insert tag sequence. However any given read may or may not extend completely through the junction code, the right insert tag sequence, and the terminal (right) barcode (if present), and molecular identity code. ILLUMINA output is composed of two reads (FIG. 7C), one from each end of the original fragment. Read 1 and Read 2 will always begin with the right or left (respectively) molecular identity code and barcode (if present). Depending on the length of the fragment, the junction code may be found only in Read 1, only in Read 2, in both Read 1 and Read 2, or not at all. Therefore, slightly different versions of the scripts are required for each platform.

ION TORRENT PGM Analysis.

Analysis of the ION TORRENT raw sequence output begins with examination of each read for the presence of specific barcodes, if present. Reads are sorted by barcode. The reads are also sorted according to the presence of the barcode at both ends of the read (likely to be true mate-pair reads), and those with only one barcode present (still usable as single-ended reads pending further processing). Reads with no detectable barcodes are saved as unsorted reads and excluded from further analysis. Next, reads with two barcodes are examined for the presence of molecular identity codes at both ends, and further separated into true mates, chimeras, etc. Finally, the true-mate reads are examined for the junction code and split into left and right di-tag sequences, labelled as 'R1' and 'R2'. For compatibility with downstream assembly software, the right di-tag sequence is reverse-complemented and its associated quality string is reversed. The sequences are also trimmed to remove the molecular identity code, barcode, and junction code sequences. The end result is paired di-tag sequences in "FR" (forward/reverse) orientation, in which the di-tags locations in the genomic sequence are separated by the distance of the fragment size used in library construction.

ILLUMINA MISEQ or HISEQ Analysis.

Output from ILLUMINA instruments is typically already de-multiplexed by ILLUMINA index code/barcode during instrument processing. Analysis of the barcode-sorted reads begins with examination of each pair of reads, Read 1 and Read 2, representing the ends of the original DNA fragment, for the presence of molecular identity codes. Read 1 is examined for the sense molecular identity codes, while Read 2 is examined for the antisense molecular identity codes. Both reads are preserved as true mates if matching molecular identity codes are found in Read 1 and Read 2. Chimeras will be discarded when mis-matched molecular identity codes are detected, and read pairs with only one molecular identity code detected will be preserved for possible use as single-end reads. Next, true mates and potential single-ended reads will be examined for the presence of the junction code and trimmed accordingly. Only true mate-pair di-tag sequences will be preserved as Read 1/Read 2 pairs. Single-ended di-tag reads from both Read 1 and Read 2 will be combined into one output file.

Sequence Data from E. coli DH10B Mate-Pair Libraries.

Table 2 illustrates the detection of chimeras and true mates among ION TORRENT reads from the E. coli DH10B 2-kb mate pair library.

TABLE 2

Molecular identity tag (MIT) analysis of 2-kb E. coli mate-pair library

| MIT | B | D | F | H | J | L | N |
|---|---|---|---|---|---|---|---|
| A | 176453 | 445 | 764 | 637 | 345 | 540 | 405 |
| C | 784 | 192818 | 534 | 900 | 656 | 586 | 507 |
| E | 15762 | 654 | 164965 | 422 | 430 | 427 | 260 |
| G | 837 | 709 | 334 | 176276 | 405 | 448 | 559 |
| I | 629 | 371 | 357 | 846 | 183403 | 710 | 519 |
| K | 507 | 546 | 854 | 482 | 1163 | 186006 | 668 |
| M | 347 | 423 | 542 | 568 | 372 | 562 | 165045 |
| O | 399 | 853 | 1739 | 698 | 730 | 998 | 335 |
| Q | 243 | 738 | 624 | 488 | 692 | 306 | 348 |
| S | 326 | 492 | 225 | 665 | 393 | 323 | 589 |
| U | 222 | 295 | 197 | 269 | 302 | 553 | 456 |
| W | 500 | 688 | 434 | 611 | 932 | 370 | 960 |

TABLE 2-continued

Molecular identity tag (MIT) analysis of 2-kb E. coli mate-pair library

| MIT | P | R | T | V | X |
|---|---|---|---|---|---|
| A | 442 | 220 | 347 | 953 | 776 |
| C | 701 | 452 | 565 | 553 | 540 |
| E | 3431 | 392 | 289 | 365 | 482 |
| G | 561 | 211 | 440 | 547 | 857 |
| I | 537 | 564 | 318 | 217 | 8914 |
| K | 796 | 340 | 363 | 426 | 1320 |
| M | 550 | 338 | 456 | 277 | 313 |
| O | <u>174758</u> | 545 | 330 | 450 | 596 |
| Q | 509 | <u>161728</u> | 348 | 178 | 537 |
| S | 356 | 723 | <u>165865</u> | 548 | 819 |
| U | 383 | 350 | 603 | <u>152305</u> | 159 |
| W | 623 | 451 | 292 | 557 | <u>171645</u> |

Diagonal cells (underlined) are true mates, totaling 2,071,267 reads. Other cells are chimera (mis-matched molecular identity codes found in one read, e.g., MIT A and MIT D in one read), totaling 96,019 reads.

Figure 9A:
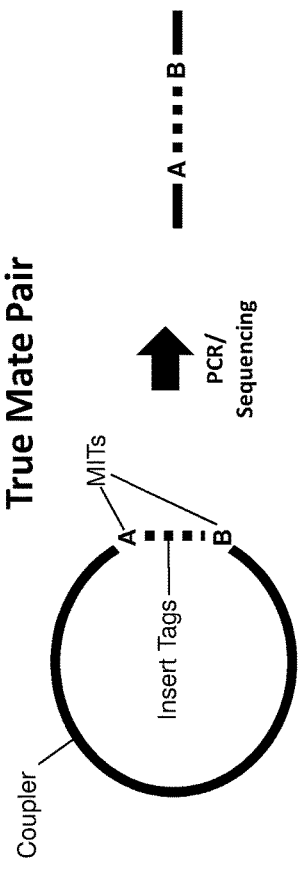
FIG. 9A is a schema depicting the generation of a true mate pair sequence from an intramolecularly circularized coupler comprising juxtaposed paired molecular identity tags.
Figure 9B:
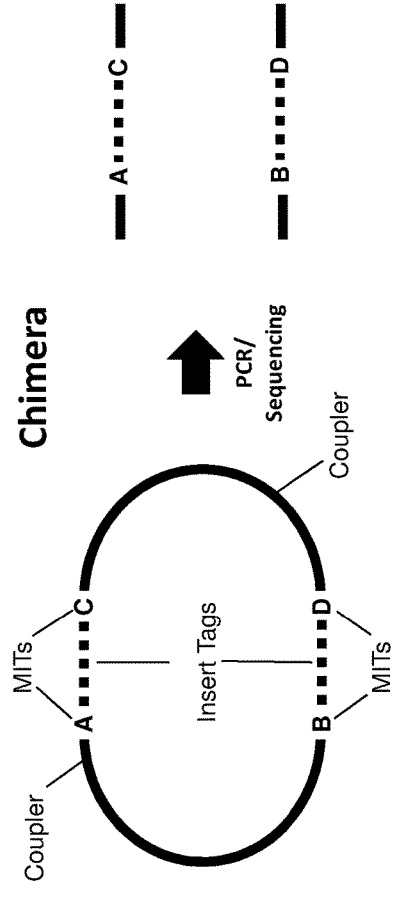
FIG. 9B is a schema depicting the generation of a chimeric sequence from intermolecularly circularized couplers comprising juxtaposed non-paired molecular identity tags.

Table 3 characterizes the ION TORRENT and ILLUMINA reads from the 2-kb and 5-kb E. coli mate pair libraries. FIG. 9A shows a schema of an intramolecular DNA species and the resulting true mate-pair sequence resulting therefrom. FIG. 9B shows a schema of an intermolecular DNA species and the resulting chimeric sequence resulting therefrom. FIG. 10A shows an example of a sequence read (SEQ ID NO:7) of a true mate pair. FIG. 10B shows an example of a sequence read (SEQ ID NO:8) from a chimera.

TABLE 3

Representative ION TORRENT PGM and ILLUMINA MISEQ data from the E coli DH10b mate pair libraries.

|  | 2 kb Ion Torrent | 5 kb Ion Torrent | 5 kb Illumina |
|---|---|---|---|
| Raw reads | 6,377,792 | 6,838,910 | 8,242,163 |
| Mates | 2,167,286 | 3,314,127 | 8,242,163 |
| True mates | 2,071,267 | 3,103,186 | 7,745,684 |
| Chimera | 96,019 | 210,940 | 496,479 |
| Split true mates | 1,825,861 | 2,769,114 | 6,992,823 |
| Average mate pair distance (bases) | 2543 | 5145 | 3922 |

REFERENCES

The following as, well as all other articles, patents, and published applications mentioned throughout this application, are incorporated by reference:

Albertson D G and Pinkel D, 2003. Genomic microarrays in human genetic disease and cancer. *Hum Mol Gen* 12 Spec No 2: R145-R152.
Albertson D G et al, 2000. Quantitative mapping of amplicon structure by array CGH identifies CYP24 as a candidate oncogene. *Nat Genet* 25: 144-146.
Andersson L, 2001. Genetic dissection of phenotypic diversity in farm animals. *Nat Rev* 2: 130-138.
Bailey A B et al, 2002. Recent segmental duplications in the human genome. *Science* 297: 1003-1007.
Batzoglou S et al, 2002. ARACHNE: A whole-genome shotgun assembler. *Genome Res* 12: 177-189.
Berka J et al, 2006. Paired end sequencing. U.S. Patent Application No US 2006/0292611.
Bignell G R et al, 2004. High-resolution analysis of DNA copy number using oligonucleotide microarrays. Genome Res 14: 287-295.
Bolivar F et al, 1977. Construction and characterization of new cloning vehicles. II multipurpose system. *Gene* 2: 95-113.
Brennan C et al, 2004. High-resolution global profiling of genomic alterations with long oligonucleotide microarray. *Cancer Res* 64: 4744-4748.
Bujnicki J M, 2001. Understanding the evolution of restriction-modification systems: Clues from sequence and structure comparisons. *Acta Biochimica Polonica* 48: 935-967.
Buryanov Y I et al, 1978. Site specific and chromatographics properties of E coli K12 and Eco RII DNA-cytosine methylases. *FEBS Lett* 88: 251-254.
Chang A C Y and Cohen S N, 1978. Construction and characterization of amplifiable multicopy DNA cloning vehicles derived from the P15A cryptic miniplasmid. *J Bacteriology* 134: 1141-1156.
Check E, 2005. Patchwork people. Nature 437: 1084-1096.
Cheng Z et al, 2005. A genome-wide comparison of recent chimpanzee and human segmental duplications. *Nature* 437: 88-93.
Collins F S et al, 1987. Construction of a general human chromosome jumping library, with application in cystic fibrosis. *Science* 235: 1046-1049.
Collins F S and Weissman S M, 1984. Directional cloning of DNA fragments at a large distance from an initial probe: A circularization method. *Proc Natl Acad Sci* (USA) 81: 6812-6816.
Craddock N and Jones I, 2001. Molecular genetics of bipolar disorder. *Br J Psychiatry* Suppl 41: S128-S133.
Deininger P L, 1983. Random subcloning of sonicated DNA: Application to shotgun DNA sequence analysis. *Analyt Biochem* 129: 216-223.
Dugaiczyk A et al, 1975. Ligation of Eco RI endonuclease-generated DNA fragments into linear and circular structures. *J Mol Biol* 96: 171-178.
Dunn J L et al, 2002. Genomic signature tags (GSTs): A system for profiling genomics DNA. *Genome Res* 12: 1756-1765.
Edwards A et al, 1990. Automated DNA sequencing of the human HPRT locus. *Genomics* 6: 593-608.
Feng T et al, 2002. Increased efficiency of cloning large DNA fragments using a lower copy number plasmid. *BioTechniques* 32: 992-998.
Feuk L et al, 2006. Structural variation in the human genome. Nature Rev 7: 85-97.
Fitzgerald M C et al, 1992. Rapid shotgun cloning utilizing the two base recognition endonuclease *CviJI Nuc Acid Res* 20: 3753-3762.
Geier G E and Modrich P, 1979. Recognition sequence of the dam methylase of *Escherichia coli* K12 and mode of cleavage of Dpn I endonuclease. *J Biol Chem* 254: 1408-1413.

Gonzalez E et al, 2005. The influence of CCL3L 1 gene-containing segmental duplications on HIV-1/AIDS susceptibility. *Science* 307: 1434-1440.

Gray J W and Collins C, 2000. Genome changes and gene expression in human solid tumors. *Carcinogenesis* 21: 443-452.

Grindley N D F and Joyce C M, 1980. Genetic and DNA sequence analysis of the kanamycin resistance transposon Tn903. *Proc Natl Acad Sci* (USA) 77: 7176-7180.

Hamelin C and Yelle J, 1990. Gel and buffer effects on the migration of DNA molecules in agarose. *Appl Theor Electrophor* I: 225-231.

Hartman S et al, 1978. Sequence specificity of the P1 modification methylase (M.Eco P1) and the DNA methylase (M. Eco dam) controlled by the *Escherichia coli* dam gene. *J Mol Biol* 126: 367-380.

Havlak P et al, 2004. The atlas genome assembly system. *Genome Res* 14: 721-732.

Hayashi K et al, 1986. Regulation of inter- and intermolecular ligation with T4 DNA ligase in the presence of polyethylene glycol. *Nuc Acids Res* 14: 7617-7630.

Heffron F et al, 1978. In vitro mutagenesis of a circular DNA molecule by using synthetic restriction sites. *Proc Natl Acad Sci* (USA) 74: 6012-6016.

Heiskanen M A et al, 2000. Detection of gene amplification by genomic hybridization to cDNA microarrays. *Cancer Res* 60: 799-802.

Holzman P S and Matthysse S, 1990. The genetics of schizophrenia: A review. *Pyschol Sci* 1: 179-286.

Huang J et al, 2004. Whole genome DNA copy number changes by high density oligonucleotides arrays. *Hum Genomics* 1: 287-299.

Huang X et al, 2006. Application of a superword array in genome assembly. *Nuc Acids Res* 34: 201-205.

Huang X et al, 2003. PCAP: A whole-genome assembly program. *Genome Res* 13: 2164-2170.

Inazawa J et al, 2004. Comparative genomic hybridization (CGH)-arrays pave the way for identification of novel cancer-related genes. *Cancer Sci* 95: 559-563.

Jaffe D B et al, 2003. Whole-genome sequence assembly for mammalian genomes: ARACHNE 2. *Genome Res* 13: 91-96.

Kan N C et al, 1979. The nucleotide sequence recognized by the *Escherichia coli* K12 restriction and modification enzymes. *J Mol Biol* 130: 191-209.

Kinzler K W et al, 1995. Method for serial analysis of gene expression. U.S. Pat. No. 5,695,937 (Issued Dec. 9, 1997).

Korbel J O et al, 2007. Paired-end mapping reveals extensive structure variation in the Human genome. *Science* 318: 420-426.

Kozdroj J and van Elsas J D, 2001. Structural diversity of microorganisms in chemically perturbed soil assessed by molecular and cytochemical approaches. *J Microl Meth* 43: 187-212.

Lok S, 2001. Methods for generating a continuous nucleotide sequence from non-contiguous nucleotide sequences. U.S. Pat. No. 6,730,500 (Issued May 4, 2004).

Lok S, 2009. Methods for nucleic acid mapping and identification of fine-structural-variations in nucleic acids. U.S. Pat. No. 8,329,400 (Issued Dec. 11, 2012).

Lok S, 2011. Methods for nucleic acid mapping and identification of fine-structural-variations in nucleic acids and utilities. U.S. Pat. No. 7,932,029 (Issued Apr. 26, 2011).

Lucito R et al, 2003. Representational oligonucleotide microarray analysis: A high-resolution method to detect genome copy number variation. *Genome Res* 13: 2291-2305.

Mackay T F C, 2001. Quantitative trait loci in *Drosophila*. *Nat Rev Genet* 2:11-20.

Mahairas G G et al, 1999. Sequence-tagged connectors: A sequence approach to mapping and scanning the human genome. *Proc Natl Acad Sci* (USA) 96: 9739-9744.

Mardis E R, 2008. Next-generation DNA sequencing methods. *Annu Rev Genomics Hum Genet* 9: 387-402.

Margulies M et al, 2005. Genome sequencing in microfabricated high-density picroliter reactors. *Nature* 437: 376-380.

Matsumura H et al, 2003. Gene expression analysis of plant host-pathogen interactions by SuperSAGE. *Proc Natl Acad Sci* (USA) 100: 15718-15723.

May M A and Hattman S, 1975. Analysis of bacteriophage deoxyribonucleic acid sequences methylated by host- and R-factor-controlled enzymes. *J Bacteriology* 123: 768-770.

McClelland M et al, 1994. Effect of site-specific modification on restriction endonucleases and DNA modification methyltransferases. *Nuc Acids Res* 22: 3640-3659.

Mead, D A and Godiska R, 2001. Cloning vectors and vector components. U.S. Pat. No. 6,709,861 (Issued Mar. 23, 2004).

Mclgar E and Goldthwait D A, 1968. Deoxyribonucleic acid nucleases: II. The effect of metals on the mechanism of action of deoxyribonuclease 1. *J Biol Chem* 243: 4409-4416.

Morozova O, Marra M A, 2008. Applications of the next-generation sequencing technologies in functional genomics. *Genomics* 92: 255-262.

Mullikin J C and Ning Z, 2003. The PHU SION assembler. *Genome Res* 13: 81-90.

Myers E W et al, 2000. A whole-genome assembly of *Drosophila*. *Science* 287: 2196-21204.

Ng P et al, 2005. Gene identification signature (GIS) analysis for transcriptome characterization and genome annotation. *Nat Meth* 2: 105-111.

Owen M J and Craddock N, 1996. Modem molecular genetic approaches to complex traits: Implications for psychiatric disorders. *Mol Psychiatry* 1: 21-26.

Patterson and Gabriel, 2009. Combinatorics and next-generation sequencing. *Nature Biotechnology* 27:826-827.

Pevzner P A and Tang H, 2001. Fragment assembly with double-barreled data. *Bioinformatics* 17 Suppl 1: S225-S233.

Pheiffer B H and Zimmerman S B, 1983. Polymer-stimulated ligation: Enhanced blunt- or cohesive-end ligation of DNA or deoxyribooligonucleotides by T4 DNA ligase in polymer solutions. *Nuc Acids Res* 11: 7853-7871.

Pinkel D and Albertson D G, 2005. Array comparative genomic hybridization and its application in cancer. *Nat Genet* Suppl 37: S11-S17.

Pinkel D et al, 1998. High resolution analysis of DNA copy number variation using comparative genomic hybridization to microarrays. *Nat Genet* 20: 207-211.

Pinkel D et al, 1997. Comparative genomic hybridization. U.S. Pat. No. 6,159,685 (Issued Dec. 12, 2000).

Pinkel D et al, 1994. Comparative fluorescence hybridization to nucleic acid arrays. U.S. Pat. No. 5,830,645 (Issued Nov. 3, 1998).

Pollack J R et al, 2002. Microarray analysis reveals a major direct role of DNA copy number alternation in the transcriptional program of human breast tumors. *Proc Natl Acad Sci* (USA) 99: 12963-12968.

Pollack J R et al, 1999. Genome-wide analysis of DNA copy-number changes using cDNA microarrays. *Nat Genet* 23: 41-46.

Pop M et al, 2004. Comparative genome assembly. Briefings in Bioinformatics 5: 237-248.
Redon R et al, 2006. Global variation in copy number in the human genome. *Nature* 444: 444-454.
Rouillard, J-M et al, 2001. Virtual genome scan: A tool for restriction landmark-based scanning of the human genome. *Genome Res* 11: 1453-1459.
Saha S et al, 2002. Using the transcriptome to annotate the genome. *Nat Biotech* 19: 508-512.
Salzberg S L and Yorke J A, 2005. Beware of mis-assembled genomes. *Bioinformatics* 21: 43204321.
Sanger F et al, 1977. DNA sequencing with chain terminating inhibitors. *Proc Natl Acad Sci* (USA) 74: 5463-5467.
Schloter M et al, 2000. Ecology and evolution of bacterial microdiversity. *FEMS Micobiol Rev* 21: 647-660.
Schriefer L A et al, 1990. Low pressure DNA shearing: A method for random DNA sequence analysis. *Nuc Acids Res* 18: 7455.
Sistla S and Rao D N, 2004. S-adenosyl-L-methionine-dependent restriction enzymes. *Crit Rev Biochem Mol Biol* 39:1-19.
Snijders A M et al, 2001. Assembly of microarrays for genome-wide measurement of DNA copy numbers. *Nat Genet* 29: 263-264.
Szybalski W, 1997. Conditionally amplifiable BAC vector. U.S. Pat. No. 5,874,259 (Issued Feb. 23, 1999).
Szybalski E et al, 1991. Class-IIS restriction enzymes-A review. Gene 100: 13-26.
Tao Q and Zhang, H-B, 1998. Cloning and stable maintenance of DNA fragments over 300 kb in *Escherichia coli* with conventional plasmid-based vectors. *Nuc Acids Res* 21: 4901-4909.
Tuzun E et al, 2005. Fine-scale structural variation of the human genome. *Nat Genet* 37: 727-732.
Velculescu V E et al, 1995. Serial analysis of gene expression. *Science* 270: 484-487.
Volik S et al, 2006. Decoding the fine-scale structure of a breast cancer genome and transcriptome. *Genome Res* 16: 394-404.
Wang J C and Davidson N, 1966. On the probability of ring closure of lambda DNA. *J Mol Biol* 19: 469-482.
Warren R L et al, 2006. Physical map-assisted whole-genome shotgun sequence assemblies. *Genome Res* 16: 768-775.
Wei C-L et al, 2004. 5' long serial analysis of gene expression (LongSAGE) and 3' LongSAGE for transcriptome characterization and genome annotation. *Proc Natl Acad Sci* (USA) 101: 11701-11706.
Weinstock G M et al, 2006. Insights into social insects from the genome of the honeybee *Apis mellifera*. *Nature* 443: 931-949.
Wimmer K et al, 2002. Combined restriction landmark genomic scanning and virtual genome scans identify a novel human homeobox gene, ALX3, that is hypermethylated in neuroblastoma. *Genes Chromosomes & Cancer* 33: 285-294.
Zhang Z et al, 2000. A greedy algorithm for aligning DNA sequencing. I *Computational Biol* 7: 203-214.
Zhao S, 2000. Human BAC ends. Nuc Acids Res 28: 129-132.
Zimmerman S B and Pheiffer B H, 1983. Macromolecular crowding allows blunt-end ligation by DNA ligases from rat liver or *Escherichia coli*. *Proc Natl Acad Sci* (USA) 80: 5852-5856.

What is claimed is:

1. A method of identifying intermolecular ligation products, comprising:

marking linear target nucleic acids with multiple, mutually distinguishable pairs of molecular identity tags to yield marked target nucleic acids, wherein the marking comprises marking terminal regions of each linear target nucleic acid with one of the pairs of molecular identity tags, wherein a first terminal region of each target nucleic acid is marked with a first member of the one of the pairs and a second terminal region of each target nucleic acid is marked with a second member of the one of the pairs;

joining terminal ends of the marked target nucleic acids or products of the marked target nucleic acids to yield marked nucleic acid products, each marked nucleic acid product comprising two of the molecular identity tags juxtaposed across the joined terminal ends, wherein the marked nucleic acid products include one or more marked nucleic acid products comprising only juxtaposed paired molecular identity tags and one or more marked nucleic acid products comprising juxtaposed unpaired molecular identity tags, wherein any marked nucleic acid product comprising juxtaposed unpaired molecular identity tags constitutes an intermolecular nucleic acid product; and parsing the one or more marked nucleic acid products comprising only juxtaposed paired molecular identity tags, or products thereof, from the one or more marked nucleic acid products comprising juxtaposed unpaired molecular identity tags, or products thereof.

2. The method of claim 1 wherein the parsing comprises sequencing the marked nucleic acid products or products thereof.

3. A method of identifying intermolecular ligation products, comprising:

marking linear target nucleic acids with multiple, mutually distinguishable pairs of molecular identity tags to yield marked target nucleic acids, wherein the marking comprises marking terminal regions of each linear target nucleic acid with one of the pairs of molecular identity tags, wherein a first terminal region of each target nucleic acid is marked with a first member of the one of the pairs and a second terminal region of each target nucleic acid is marked with a second member of the one of the pairs;

joining terminal ends of the marked target nucleic acids or products of the marked target nucleic acids to yield circularized, marked nucleic acid products, each marked nucleic acid product comprising two of the molecular identity tags juxtaposed across the joined terminal ends, wherein any marked nucleic acid product comprising juxtaposed unpaired molecular identity tags constitutes an intermolecular nucleic acid product;

linearizing the circularized, marked nucleic acid products to yield one or more linearized, marked nucleic acids comprising only juxtaposed paired molecular identity tags and one or more linearized, marked nucleic acids comprising juxtaposed unpaired molecular identity tags; and parsing the one or more linearized, marked nucleic acids comprising only juxtaposed paired molecular identity tags from the one or more linearized, marked nucleic acids comprising juxtaposed unpaired molecular identity tags.

4. The method of claim 3 wherein the linearizing is selected from the group consisting of fragmenting the circularized, marked nucleic acids and amplifying linear portions of the circularized, marked nucleic acids.

5. A method of identifying intermolecular ligation products, comprising:

marking linear target nucleic acids with multiple, mutually distinguishable pairs of molecular identity tags to yield marked target nucleic acids, wherein the marking comprises marking terminal regions of each linear target nucleic acid with one of the pairs of molecular identity tags, wherein a first terminal region of each target nucleic acid is marked with a first member of the one of the pairs and a second terminal region of each target nucleic acid is marked with a second member of the one of the pairs; and joining terminal ends of the marked target nucleic acids or products of the marked target nucleic acids to yield marked nucleic acid products, each marked nucleic acid product comprising two of the molecular identity tags juxtaposed across the joined terminal ends, wherein any marked nucleic acid product comprising juxtaposed unpaired molecular identity tags constitutes an intermolecular nucleic acid product, wherein:
each pair of molecular identity tags is physically linked;

the marking comprises marking the terminal regions of each linear target nucleic acid with one of the physically linked pairs of molecular identity tags to yield end-coupled, marked target nucleic acids, wherein the physically linked pairs of molecular identity tags are physically linked prior to and during the marking;

the method further comprises excising a target nucleic acid portion from each of the end-coupled, marked target nucleic acids to yield sequence-excised, marked target nucleic acids; and the joining comprises circularizing the sequence-excised, marked target nucleic acids to yield the marked nucleic acid products.

6. The method of claim 5 wherein the marking comprises marking the linear target nucleic acids with a plurality of nucleic acids, each of the plurality of nucleic acids comprising:

at least a first nucleic acid strand, the first nucleic acid strand on each of the plurality of nucleic acids comprising:
a first molecular identity tag;
a first primer-binding site;
a second molecular identity tag; and
a reverse complement of a second primer-binding site;
wherein:
the first molecular identity tag is located on the first nucleic acid strand in a 5' position with respect to the first primer-binding site;
the second molecular identity tag is located on the first nucleic acid strand in a 3' position with respect to the reverse complement of the second primer-binding site; and
the first molecular identity tag and the first primer-binding site are located on the first nucleic acid strand in a 5' position with respect to the second molecular identity tag and the reverse complement of the second primer-binding site;

wherein:
the first primer-binding sites in the plurality of nucleic acids are identical or substantially identical with each other;
the reverse complements of the second primer-binding sites in the plurality of nucleic acids are identical or substantially identical with each other;
the first molecular identity tags in a set of at least two of the plurality of nucleic acids are distinguishable from each other; and
the second molecular identity tags in the set of the plurality of nucleic acids are distinguishable from each other.

7. The method of claim 1 wherein the marking comprises marking the terminal regions of each linear target nucleic acid with non-physically linked pairs of molecular identity tags.

8. The method of claim 7 wherein the marking the terminal regions of each linear target nucleic acid with non-physically linked pairs of molecular identity tags comprises:
dividing the linear target nucleic acids into first aliquots;
terminally attaching a different partial molecular identity tag to the divided target nucleic acids in each first aliquot to generate partially marked target nucleic acids;
pooling the partially marked target nucleic acids;
dividing the pooled, partially marked target nucleic acids into second aliquots; and
terminally attaching a different partial molecular identity tag to the divided, partially marked target nucleic acids in each second aliquot to generate the marked target nucleic acids.

9. The method of claim 1 wherein the joining further includes inserting a nucleic acid comprising a junction code between the joined terminal ends of the marked target nucleic acids or products of the marked target nucleic acids.

10. The method of claim 1 wherein the marking comprises marking the linear target nucleic acids with a plurality of nucleic acids, each of the plurality of nucleic acids comprising:
at least a first nucleic acid strand, the first nucleic acid strand on each of the plurality of nucleic acids comprising:
a first molecular identity tag;
a first primer-binding site;
a second molecular identity tag; and
a reverse complement of a second primer-binding site;
wherein:
the first molecular identity tag is located on the first nucleic acid strand in a 5' position with respect to the first primer-binding site;
the second molecular identity tag is located on the first nucleic acid strand in a 3' position with respect to the reverse complement of the second primer-binding site; and
the first molecular identity tag and the first primer-binding site are located on the first nucleic acid strand in a 5' position with respect to the second molecular identity tag and the reverse complement of the second primer-binding site;
wherein:
the first primer-binding sites in the plurality of nucleic acids are identical or substantially identical with each other;
the reverse complements of the second primer-binding sites in the plurality of nucleic acids are identical or substantially identical with each other;
the first molecular identity tags in a set of at least two of the plurality of nucleic acids are distinguishable from each other; and
the second molecular identity tags in the set of the plurality of nucleic acids are distinguishable from each other.

11. The method of claim 10 wherein the plurality of nucleic acids comprise multiple copies of each of the at least two of the plurality of nucleic acids in the set, wherein each copy is a nucleic acid with a sequence identical to one of the at least two of the plurality of nucleic acids in the set.

12. The method of claim 10 wherein each of the plurality of nucleic acids is a linear nucleic acid including a first terminus and a second terminus.

13. The method of claim 12, wherein the first molecular identity tag is located between the first terminus and the second molecular identity tag, and the second molecular identity tag is located between the second terminus and the first molecular identity tag.

14. The method of claim 13 wherein each of the first nucleic acid strands comprises from 0 to about 90 bases between a 5' end of the first molecular identity tag and the first terminus, and further comprises from 0 to about 90 bases between the second terminus and a 3' end of the second molecular identity tag.

15. The method of claim 13 wherein each of the first nucleic acid strands comprises from 2 to about 100 bases between a 5' end of the first primer-binding site and the first terminus, and further comprises from 2 to about 100 bases between the second terminus and a 3' end of the reverse complement of the second primer-binding site.

16. The method of claim 10 wherein each of the first nucleic acid strands comprises from about 30 bases to about 10 kilobases.

17. The method of claim 10 wherein the first molecular identity tags and the second molecular identity tags each independently have a length of from about 2 to about 30 bases.

18. The method of claim 10 wherein each of the plurality of nucleic acids includes a second nucleic acid strand that comprises a reverse complement of the first molecular identity tag, a reverse complement of the first primer-binding site, the second primer-binding site, and a reverse complement of the second molecular identity tag.

19. The method of claim 10 wherein the set of the nucleic acids includes at least 10 of the plurality of nucleic acids, wherein the first molecular identity tags in each of the at least 10 of the plurality of nucleic acids in the set are distinguishable from each other, and wherein the second molecular identity tags in each of the at least 10 of the plurality of nucleic acids in the set are distinguishable from each other.

* * * * *

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Sequence Adapter

<400> SEQUENCE: 1
ccatctcatc cctgcgtgtc tccgactcag                                         30

<210> SEQ ID NO 2
<211> LENGTH: 41
<212> TYPE: DNA
<213> ORGANISM: Artificial Sequence
<220> FEATURE:
<223> OTHER INFORMATION: Sequence Adapter

<400> SEQUENCE: 2
atcaccgact gcccatagag aggaaagcgg aggcgtagtg g                            41

<210> SEQ ID NO 3
<211> LENGTH: 33
<212> TYPE: DNA
<213> ORGANISM: Artificial Sequence
<220> FEATURE:
<223> OTHER INFORMATION: Sequence Adapter

<400> SEQUENCE: 3
acactctttc cctacacgac gctcttccga tct                                     33
```

<210> SEQ ID NO 4
<211> LENGTH: 21
<212> TYPE: DNA
<213> ORGANISM: Artificial Sequence
<220> FEATURE:
<223> OTHER INFORMATION: Sequence Adapter

<400> SEQUENCE: 4
agatcggaag agcacacgtc t                                           21

<210> SEQ ID NO 5
<211> LENGTH: 28
<212> TYPE: DNA
<213> ORGANISM: Artificial Sequence
<220> FEATURE:
<223> OTHER INFORMATION: Junction Code Sequence

<400> SEQUENCE: 5
ggttcatcgt caggcctgac gatgaacc                                    28

<210> SEQ ID NO 6
<211> LENGTH: 2000
<212> TYPE: DNA
<213> ORGANISM: Artificial Sequence
<220> FEATURE:
<223> OTHER INFORMATION: Linker Sequence

<400> SEQUENCE: 6
acatctgggt agtcaggcaa ccctccaccc cactcacacc catagttcag tattacaccc    60
cgacacgctc actcacacga ttgttgttgt agcgacctct acaaaatcca cttgaccgca   120
taaacgggca atcgcacctt atactgacac gccgactatt ccccctttgc cctgccacta   180
cttccctctc tgtgtgctaa atgcctctaa ctctcccctc tcccactccc ctttcctcat   240
ctaatatcct gccccacccc tgacctttcg ctaacccacc ccaaccccct cacctttaga   300
ttatctcaac tcgcaccgca ggggcaacgc ctctcaaatc acagatttcg tcaatagggt   360
gctatcctcc ctccactaaa gcggttgtca gtcatacagg cgtatgcgaa acaccattct   420
ggcgaagttt cccctgaact ctcgcaccta tggactgcgt aagatttgag cattttctc    480 acagcaagaa tatactataa aggtgcttac cccctccccc tgctcatctg tgtccaaact   540
cgtttagagg cgtaagcact tacccttttca gtaagaacct ttaggttctc ggcagggcat   600
aggagtaatc tattccattc ccctgtgat actgccgaca acagacacac tctgcttcac   660
tccaagaggg cgacacctac tgacaggttc gccccatacc tctccctttt agtcgtgcta   720
ccttatatga ggaacgcctt gttccacaat actacatacc ccgtgtattt ccctctactg   780
ctctggcgtg attttattct gcggtgtcag tcaatcccata gacctgtcgg cacacttttt   840
gtttccccgt ccattaccaa aatgatgata acgagggcaa tatcgcacac aaaggcattt   900
gtagagcgtt ccacccagac gacttacaag acttccacta tatacttatc tctccctcgt   960
tcccaccgcc cctatctcgt cctgtgcgat tttcgtcaag aagtatgtca gcgtaggtgt  1020
cgcacagggt tgagtgtcgg gcagtcggcg tatctgttag tcttgtggtc gccacaagta  1080
agcaccatac caccgcatag tatagtccta cgggatagtc ataccgagtg cctcgttctc  1140
tgctacgcat aggtgggcgt tctctgtgag agcagagttt acaatgggc agacctccac    1200 caccagcgat taccaagtga taccctact atcttgccac gctttgacga agtaagaacg   1260
cataaacagg gtggggatta gttcgtccta cttgctgtcg ctttagtcgt caaaacgcac   1320
cctcgctgtg aaacgaccta ataataaccc tgacattaga ggttgctacg gggcgaatag  1380

```
aaccttatct gctacatctg tcgctctgtg ccaaccccag acgacaaact aatcgccaag    1440
cgtagcgaga ttatcgtagg cgacatttca gttggcggtt tgaaagcggt gtcctaaaag    1500
aatgtcatta ccctaatct gttggggttg ccaacatcac aaccccacgc ctctaacaga    1560
cctccttgat actgaaccaa acgattagca gggggagaaa tgcggagaat ggatagcgtg    1620
gcgtatcaca ccctcatact ctataaggtg gagtgcgtag cggtaaatgg aggtcaaaag    1680
ggtttcctta cgcaagatgt cgtggcgtga tacctacatt ccctatgaca gcgttgcgtg    1740
gcagtatttt tatcacgcac ttttgaaact tactgcctta cgggtatttg ggggttattg    1800
gcagagcaag agattacata ggggaggcaa ctctacaaca gcagttgtcg ttctaaatgt    1860
cctccccgtc ctccaccgca acaggtcggc agggagggtg gttgtcgcac tcacatctct    1920
atcttatcca aaggtcagca tagagcgaga atgtgttgtt gtcaggcggt atgctcctac    1980
cgagaaagtg atgaggaagt                                                2000

<210> SEQ ID NO 7
<211> LENGTH: 356
<212> TYPE: DNA
<213> ORGANISM: Artificial Sequence
<220> FEATURE:
<223> OTHER INFORMATION: Sequence Read

<400> SEQUENCE: 7
tggactccac tgtgtaagga gaacgatcta catggttgta ggcattgtgc cgcgcgatgc      60
gggcaacatc attattgatg atgacgatat cagtctgctg cctctgcatg cacgcgcgcg     120
ccgcggtatc ggggtacatc cgcttggcca aggcggatgt accctcgacc attcccgtcc     180
atcgattttc gcaccacagc ggagcaagca gcgtcgggcg acgggcgctg gcggaaatgc     240
ggtggtagat cacttccggt ggcgtatggc gaatcatttc tccggcagtg agcgtgtaat     300
cctccagttc aataccgttc aaacgcccat cgttctcctt acaacattgg tctgga         356

<210> SEQ ID NO 8
<211> LENGTH: 379
<212> TYPE: DNA
<213> ORGANISM: Artificial Sequence
<220> FEATURE:
<223> OTHER INFORMATION: Sequence Read

<400> SEQUENCE: 8
tggactccac tgtgtaagga gaacgatcat acgtgaattc gacggcggcg attaaagcgt      60
tcgttggacg ccgtacatc cgccttggcc aaggcggat taccgctgc ttcccggaaa       120 gaaaagttag ccggaaaaaa ccagatcggg atcattggct atgcttcgct tttttcgttc     180 tgtttttcc attttcacgt atatacatga agagaagtaa caaaaagggg gagagtttga     240
tggcttactt cggctcgaaa ggatggctcg tccaacaatt aaaagaggcg ggaattcgtt     300
ggcatcctat ggaaaggaaa aaaattgaaa ctataaaagc ggcgatttta taatcgttct     360
ccttacacat tggacttcg                                                  379
```